United States Patent
Terwey et al.

(10) Patent No.: US 10,328,238 B2
(45) Date of Patent: Jun. 25, 2019

(54) CATHETER SYSTEM

(71) Applicant: St. Jude Medical, Cardiology Division, Inc., St. Paul, MN (US)

(72) Inventors: Russell D. Terwey, St. Michael, MN (US); James Paul Goodman, Eden Prairie, MN (US); Kevin Gin Park, Golden Valley, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 775 days.

(21) Appl. No.: 14/201,141

(22) Filed: Mar. 7, 2014

(65) Prior Publication Data

US 2014/0276397 A1    Sep. 18, 2014

Related U.S. Application Data

(60) Provisional application No. 61/777,259, filed on Mar. 12, 2013, provisional application No. 61/777,249, (Continued)

(51) Int. Cl.
*A61B 18/00* (2006.01)
*A61M 25/00* (2006.01)
(Continued)

(52) U.S. Cl.
CPC ......... *A61M 25/0097* (2013.01); *A61B 18/14* (2013.01); *A61B 18/1492* (2013.01); (Continued)

(58) Field of Classification Search
CPC .............................................. A61M 25/0136
See application file for complete search history.

(56) References Cited

U.S. PATENT DOCUMENTS

| 3,650,277 A | 3/1972 | Sjostrand et al. |
| 4,658,819 A | 4/1987 | Harris et al. |

(Continued)

FOREIGN PATENT DOCUMENTS

| WO | 97/45157 | 12/1997 |
| WO | 00/66020 | 11/2000 |

(Continued)

OTHER PUBLICATIONS

Robbins, Ivan M. et al, Pulmonary Vein Stenosis After Catheter Ablation of Atrial Fibrillation, Circulation Journal of the American Heart Association, 1998;98:1769-1775.

(Continued)

*Primary Examiner* — Luther Behringer
(74) *Attorney, Agent, or Firm* — Armstrong Teasdale LLP

(57) ABSTRACT

In a catheter system and method for controlling such a system, an elongate hollow shaft has a proximal end connected to a handle and a distal end remote from the handle. A working component is carried by the shaft and has at least one characteristic that is adjustable. An actuator is rotatably mounted on the handle for selectively adjusting at least one characteristic of the working component. A control line extends at least in part within the shaft. The control line operatively couples the actuator with the working component such that rotation of the actuator relative to the handle effects linear translation of the control line to adjust the at least one characteristic of the working component.

8 Claims, 32 Drawing Sheets

Related U.S. Application Data filed on Mar. 12, 2013, provisional application No. 61/777,236, filed on Mar. 12, 2013.

(51) Int. Cl.
*A61B 18/14* (2006.01)
*A61M 25/01* (2006.01)

(52) U.S. Cl.
CPC . *A61M 25/0136* (2013.01); *A61B 2018/0091* (2013.01); *A61B 2018/00267* (2013.01); *A61B 2018/00404* (2013.01); *A61M 2025/0098* (2013.01)

(56) References Cited

U.S. PATENT DOCUMENTS

| | | |
|---|---|---|
| 5,035,694 A | 7/1991 | Kasprzyk et al. |
| 5,255,679 A | 10/1993 | Imran |
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,044 B1 | 4/2001 | Kordis |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hedge et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 9,022,948 B2 | 5/2015 | Wang |
| 2002/0068885 A1 | 6/2002 | Harhen et al. |
| 2002/0120304 A1 | 8/2002 | Mest |
| 2003/0050681 A1 | 3/2003 | Pianca et al. |
| 2003/0060803 A1 | 3/2003 | McGlinch et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0107739 A1 | 5/2005 | Palma et al. |
| 2005/0288730 A1 | 12/2005 | Deem et al. |
| 2006/0089678 A1 | 4/2006 | Shalev |
| 2007/0135875 A1 | 6/2007 | Demarais et al. |
| 2008/0255478 A1 | 10/2008 | Burdette |
| 2009/0076409 A1 | 3/2009 | Wu et al. |
| 2009/0105640 A1* | 4/2009 | Bednarek .......... A61M 25/0136 604/95.04 |
| 2010/0016762 A1 | 1/2010 | Thapliyal et al. |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2011/0004087 A1 | 1/2011 | Fish et al. |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2012/0143097 A1 | 6/2012 | Pike, Jr. |
| 2012/0143298 A1 | 6/2012 | Just et al. |
| 2012/0296232 A1 | 11/2012 | Ng |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2009/085108 | 7/2009 |
| WO | 2012002299 A1 | 1/2012 |
| WO | 2012/064818 | 5/2012 |
| WO | 2012/106492 | 8/2012 |

OTHER PUBLICATIONS

Rocha-Singh, Krishna J., Catheter-Based Sympathetic Renal Denervation a Novel Strategy for the Treatment of Resistant Hypertension, Endovascular Today, Aug. 2009, 52-56.

Rocha-Singh, Krishna J., Renal Artery Denervation: A Brave New Frontier, Endovascular Today, Feb. 2012, 45-53.

Sanderson, John E. et al, Effect of B-Blockade on Baroreceptor and Autonomic Function in Heart Failure, Clinical Science (1999) 96, 137-146.

(56) References Cited

OTHER PUBLICATIONS

Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of the American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of the American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of the American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of the American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of the American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.—Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of the American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/

(56) References Cited

OTHER PUBLICATIONS ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the SYMPLICITY HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After SYMPLICITY HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of the American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter -based Treatment for Hypertension, Symplicity RDN System Common Q&A, 2011.

(56) References Cited

OTHER PUBLICATIONS

Medtronic, Inc., Scientific Basis Behind Renal Denervation for the Control of Hypertension, Dec. 2012, http://www.icimeeting.com/2012/images/stories/PDF/1448_Wilcox_1_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of the American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.
Zazgornik, Jan et al, Bilateral Nephrectomy: The Best, but Often Overlooked, Treatment for Refractory Hypertension in Hemodialysis Patients, AJH 1998; 11:1364-1370.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of the American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5 , pp. 253-255.
Oral, Hakan et al, Pulmonary Vein Isolation for Paroxysmal and Persistent Atrial Fibrillation, Circulation Journal of the American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.

(56) References Cited

OTHER PUBLICATIONS

Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, , Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of the American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of the American Heart Association, 1999;99:319-325.
Plouin, Pierre-Francois et al, Blood Pressure Outcome of Angioplasty in Atherosclerotic Renal Artery Stenosis a Randomized Trial, Hypertension Journal of the American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"? :An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidney in Permanent Hypertensive States, The Medical Press, Feb. 22, 1936, No. 16, 307-310.

(56) References Cited

OTHER PUBLICATIONS

Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.
De Wardener, H.E., The Hypothalamus and Hypertension, Physiological Reviews, vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of the American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of the American Heart Association, vol. 41, Mar. 2003, Part II, 621-624.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of the American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of the American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:I-13 (1982).
Grassi, Guido et al, Baroreflex Control of Sympathetic Nerve Activity in Essential and Secondary Hypertension, Hypertension Journal of the American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.

(56) References Cited

OTHER PUBLICATIONS

Hall, Winthrop H. et al, Combined Embolization and Percutaneous Radiofrequency Ablation of a Solid Renal Tumor, American Journal of Roentgenology, 174, Jun. 2000, 1592-1594.

Hamm, Christian et al, Confluence, Issue eight, Apr. 2014.

Han, Young-Min et al, Renal Artery Embolization with Diluted Hot Contrast Medium: An Experimental Study, Journal of Vascular and Interventional Radiology, Jul. 2001;12(7):862-868.

Hansen, Jesper Melchoir et al, The Transplanted Human Kidney Does Not Achieve Functional Reinnervation, Clinical Science, (1994) 87, 13-20.

Heuer, George J., The Surgical Treatment of Essential Hypertension, Annals of Surgery, Oct. 1936, vol. 104, No. 3, 771-786.

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pt 2):F738-F745.

Hoobler, S.W. et al, The Effects of Splanchnicectomy on the Blood Pressure in Hypertension, Circulation Journal of the American Heart Association, vol. IV, Aug. 1951, 173-183.

Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.

Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

Huang, Shoei K. Stephen et al, Radiofrequency Catheter Ablation of Cardiac Arrhythmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of the American Heart Association, 1998;32:249-254.

Humpreys, Michael H., Renal Nerves and CKD: Is Renal Denervation the Answer?, Journal of the American Socity of Nephrology, 2012, 23: 1-3.

International Search Report and Written Opinion for Application No. PCT/US2010/054637 dated Jan. 3, 2011.

International Search Report and Written Opinion for Application No. PCT/US2010/054684 dated Jan. 10, 2011.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

\* cited by examiner

CATHETER SYSTEM

CROSS-REFERENCE TO RELATED APPLICATIONS

This application claims priority to provisional application Ser. Nos. 61/777,236, 61/777,249, and 61/777,259 filed Mar. 12, 2013, the entire specifications of which are incorporated herein.

BACKGROUND OF THE DISCLOSURE

A. Field of the Disclosure

The present disclosure relates generally to a catheter system for use in a human body, and more particularly to a catheter system having at least one selectively adjustable feature, and still more particularly to a catheter system having multiple control lines associated with multiple components of the system, at least one of which is selectively adjustable.

B. Background Art

Catheter systems are well known in the art for use in medical procedures, such as diagnostic, therapeutic and ablative procedures. Typical catheter systems generally include an elongate catheter extending from a handle. A physician manipulates the catheter through the patient's vasculature to an intended site within the patient. The catheter typically carries one or more working components, such as electrodes or other diagnostic, therapeutic or ablative devices for carrying out the procedures. Controls, or actuators may be provided on the handle for selectively adjusting one or more characteristics of the working components.

One particular example of the catheter system is an ablative catheter system in which the working component is a multi-electrode component carried at the distal end of the catheter. A control wire extends within the shaft of the catheter from the electrode component to the handle to operatively connect the electrode component to an actuator on the handle. Actuation of the actuator acts on the control wire to configure the electrode component into a desired configuration. For example, in one such ablative catheter system made by St. Jude Medical, Inc. under the trade name EnligHTN, the multi-electrode component is in the form of an electrode basket. Upon locating the electrode basket at a desired location within the patient, actuation of the actuator on the handle pulls on the control wire to reconfigure the electrode from a collapsed configuration to an expanded configuration in which the electrodes are in contact with a surface, such as an arterial wall. It is thus important to maintain proper tension in the control wire. In some catheter systems, there may be a need for two or more separate control wires, such as where there are two or more working components carried by the catheter. In such an arrangement, it is desirable that proper tension in each of the control wires be maintained, particularly when only one of the control wires is being acted upon. It is also desirable to maintain a secure connection of the catheter to the handle. It is further desirable for the physician to be able to readily actuate the actuator, and for the system to facilitate maintaining the actuator in a desired position corresponding to a desired configuration of a working component.

BRIEF SUMMARY OF THE DISCLOSURE

In one embodiment, a catheter system generally comprises a handle and an elongate hollow shaft having a proximal end connected to the handle and a distal end remote from the handle. A working component is carried by the shaft and has at least one characteristic that is adjustable. An actuator is rotatably mounted on the handle for selectively adjusting at least one characteristic of the working component. A control line extends at least in part within the shaft. The control line operatively couples the actuator with the working component such that rotation of the actuator relative to the handle effects linear translation of the control line to adjust the at least one characteristic of the working component.

In one embodiment of a method of controlling a catheter system of the type having a handle and a working component operatively coupled to the handle by a control line, the method generally comprises rotating an actuator relative to the handle, and acting on the control line in response to rotation of the actuator to effect linear translation of the control line, the linear translation of the control line adjusting at least one characteristic of the working component.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
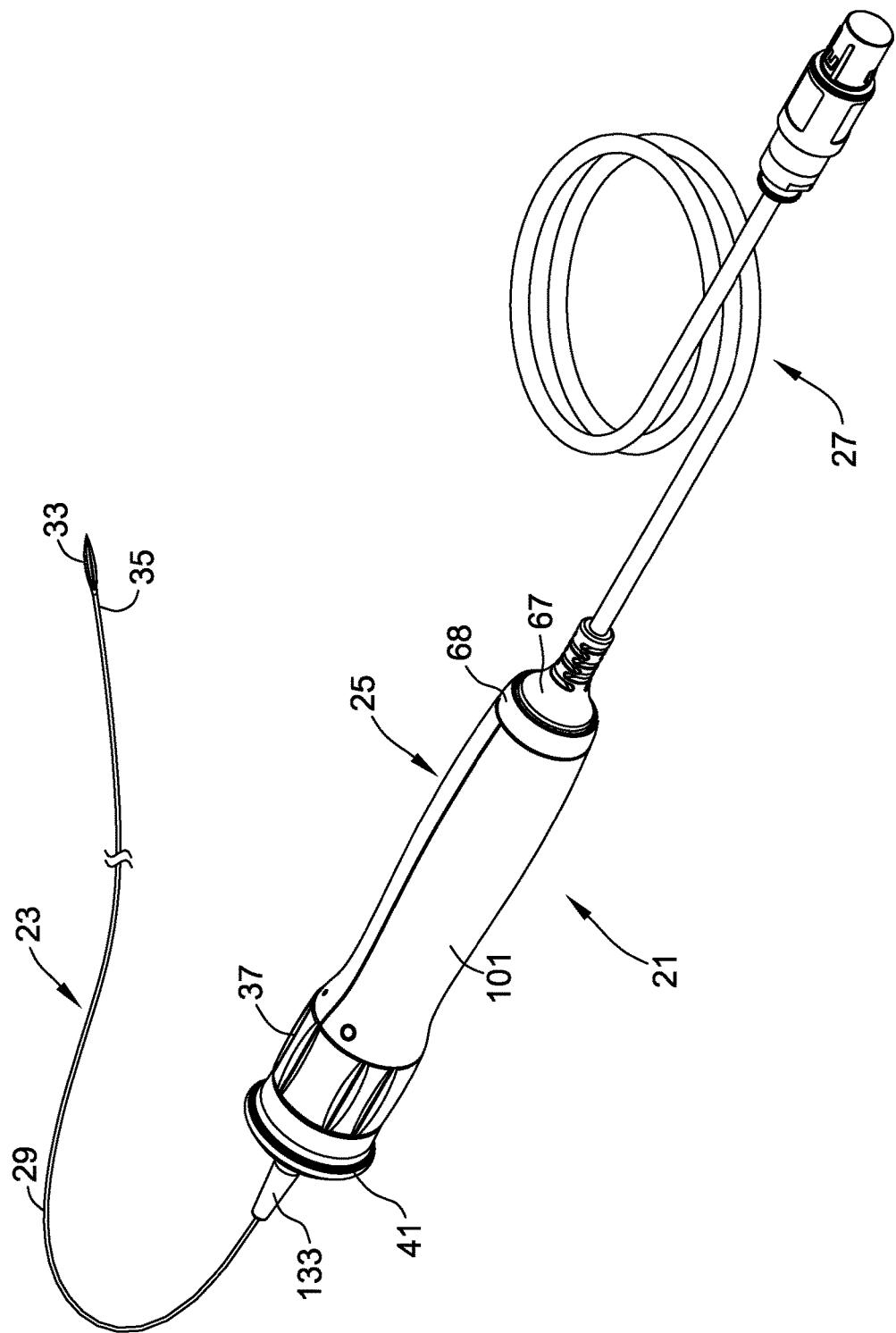
FIG. 1 is a perspective view of one embodiment of a catheter system.
Figure 2:
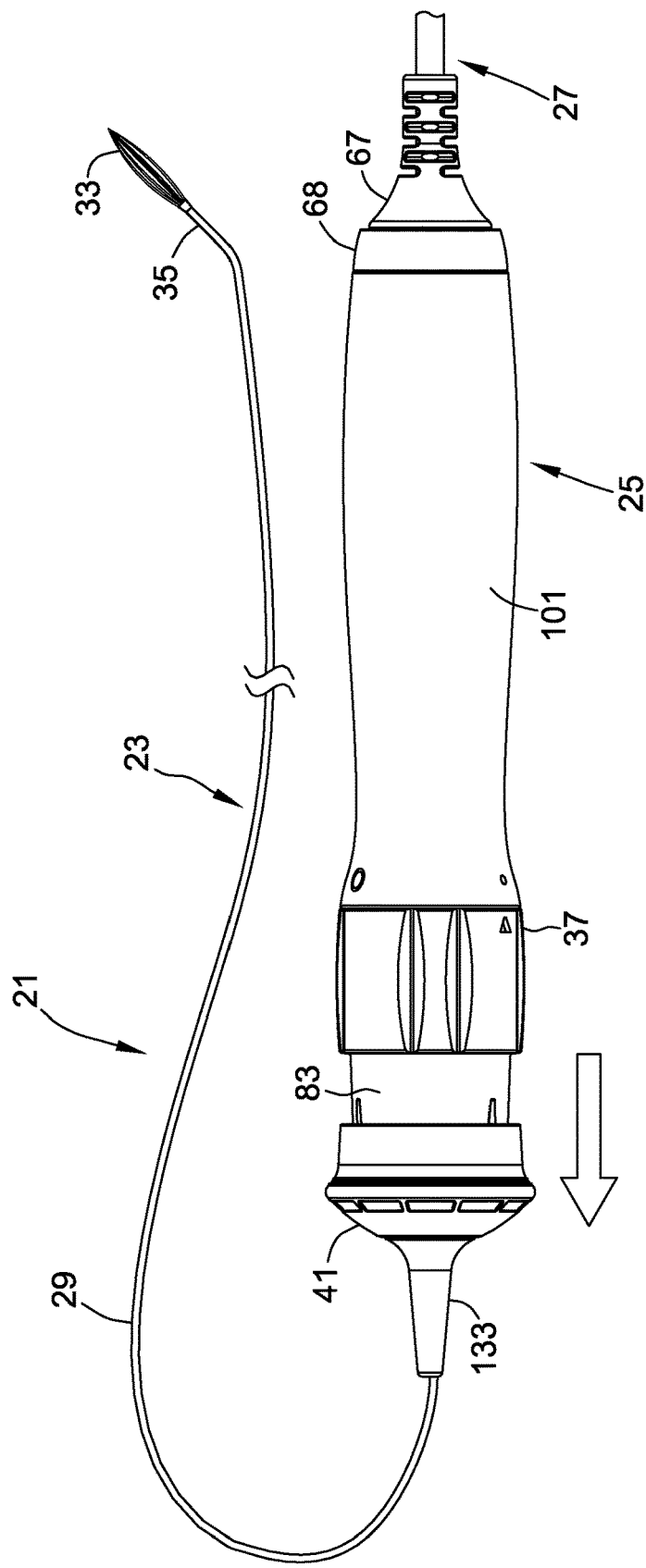
FIG. 2 is a side elevation of a catheter and handle of the catheter system of FIG. 1, with a distal or front end segment of a catheter shaft deflected relative to the remainder of the catheter shaft and with a slide actuator in its extended or actuated position corresponding to the deflection of the catheter shaft.

Referring now to the drawings, and in particular to FIGS. 1 and 2, one embodiment of a catheter system is indicated generally at 21 and includes a catheter 23, a handle 25 to which the catheter is connected, and a conductor assembly 27 for electrically connecting the catheter system to a suitable power supply (not shown).

In the embodiments illustrated and described herein, the catheter system 21 includes an elongate flexible catheter 23 that is also selectively deflectable (e.g., bendable)—such as at or adjacent the end or tip, broadly referred to as a first working component or first component, of the catheter—as illustrated for example in FIG. 2. The catheter system 21 also includes what is broadly referred to as a second working component (or second component). As used herein, a working component is intended to refer to any component that is used for guiding, diagnostic, therapeutic, ablative or other function relating to a patient. Working components may be carried by the catheter 23 and selectively operated or adjusted. As used in herein, selective operation or adjustment of a working component is intended to refer to a functional changing of at least one characteristic of the working component, such as changing the configuration of the component, changing the orientation of the component, supplying current to the component, inflating or collapsing the component or otherwise adjusting, manipulating or operating the component for its intended purpose.

As one example, the catheter system 21 illustrated and described herein is suitably constructed for use as an ablation system, such as a renal or heart ablation system. More particularly, the illustrated catheter system 21 is a multi-electrode renal denervation system. One example of such a system is that currently made by St. Jude Medical, Inc. under the trade name EnligHTN. General operation of a multi-electrode renal denervation system is known to those of skill in the art and is not described further herein except to the extent necessary to describe the present embodiments. It is understood that the catheter system 21 may be used for any other suitable treatment or purpose without departing from the scope of this disclosure. Additionally, while the catheter system 21 is illustrated and described herein as including only the flexible catheter, the system may further include other components used, for example, to guide the flexible catheter into the patient—such as, without limitation, a relatively more rigid guide catheter (not shown).

The illustrated catheter 23 of FIG. 1 includes an elongate, flexible hollow shaft 29 having a central passage and connected to the handle 25 at or near a proximal or rear end 31 (not visible in FIGS. 1 and 2 but seen, e.g., in FIG. 7) of the catheter shaft, and an electrode basket 33 (broadly, a working component and more broadly a second component of the catheter system) disposed at or near a distal or front end 35 (or what is sometimes referred to as the tip) of the catheter shaft. It is understood, however, that the electrode basket 33 may be disposed anywhere along the catheter shaft 29 intermediate the rear end 31 and the front end 35 thereof without departing from the scope of this disclosure.

As used herein, the terms proximal and front, and distal and rear, are used with reference to the orientation of the catheter system 21 illustrated in the various drawings and for the purpose of describing the various embodiments set forth herein, and are not intended as limiting the catheter system and related components to having any particular orientation upon assembly or during operation thereof.

Figure 3:
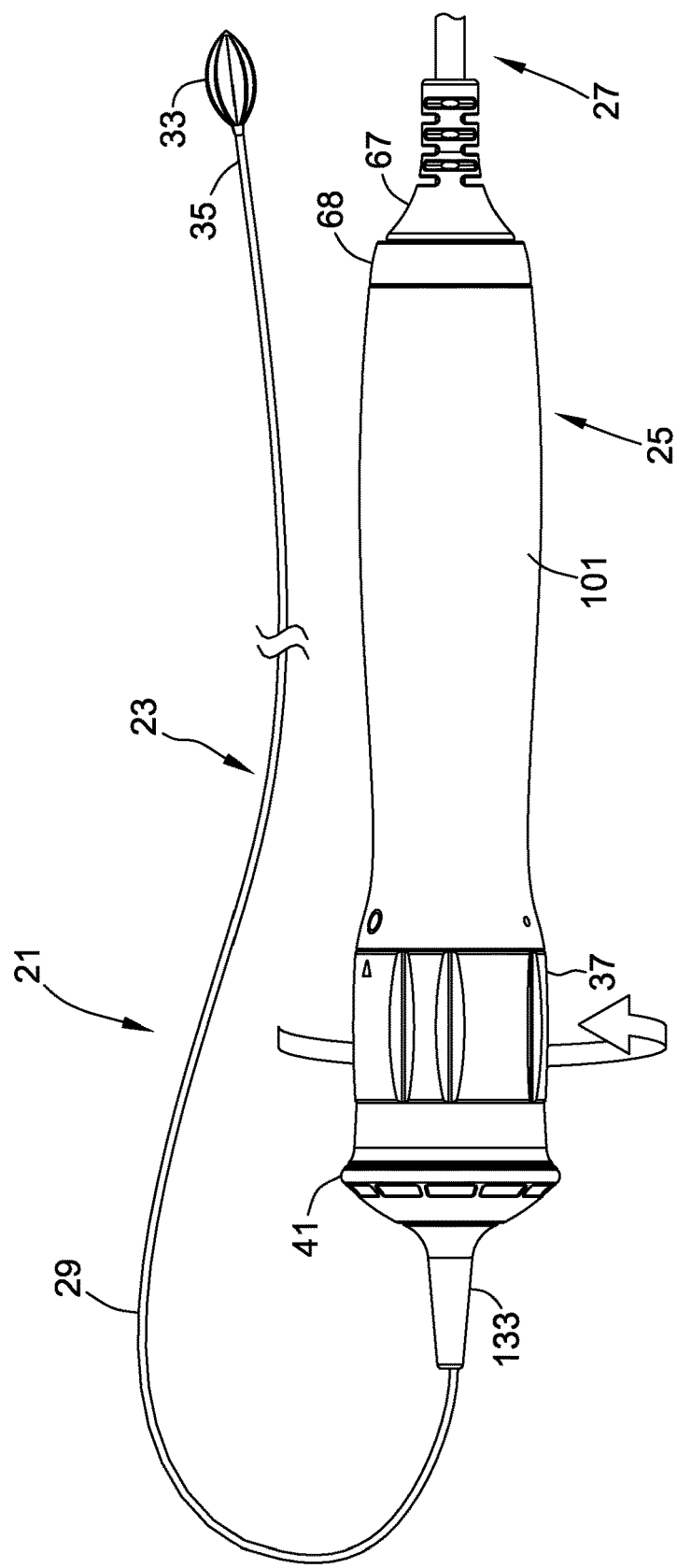
FIG. 3 is a side elevation similar to FIG. 2, but with the slide actuator in its neutral or unextend position corresponding to the catheter shaft being undeflected, and with an electrode basket of the catheter system in an expanded configuration resulting from rotation of a rotatable actuator.

The electrode basket 33 is suitably configurable between a collapsed configuration (FIG. 1) and an expanded configuration (FIG. 3). An annular (e.g., ring-shaped) actuator 37 (FIG. 3) is mounted on the handle 25 for rotation relative thereto and is operatively connected to the electrode basket 33 for selectively configuring the electrode basket between its collapsed and expanded configurations. It is understood that other suitable actuators (e.g., slide, push button, lever, etc.) may be used instead of the rotating actuator 37 to selectively configure the electrode basket 33 without departing from the scope of this disclosure. In some embodiments, the electrode basket 33 may be selectively adjustable between an infinite number of configurations between its collapsed and expanded configurations using the actuator 37. A control line, such as a suitable cable or pull wire 39 (FIG. 4), extends from the electrode basket 33 within the hollow catheter shaft 29 and into the handle 25 and operatively connects the annular actuator 37 with the electrode basket via a worm gear assembly 306 (FIG. 4 and described in further detail later herein) to which the pull wire is connected. While in the illustrated embodiment a single pull wire 39 is used to selectively configure the electrode basket, it is contemplated that two or more pull wires, cables or other suitable control lines may be used for selectively configuring the electrode basket. It is also understood that the control line may be any suitable control line other than a pull wire, such as a cable, string, tie, compression member or other suitable line useful to operatively connect the electrode basket 33 to the worm gear assembly 306 and hence the handle 25.

In the illustrated embodiment, the catheter shaft 29 is also configured for deflection near the tip or front end 35 thereof, such as between an undeflected configuration (FIG. 1) and a deflected (e.g., bent or angled) configuration (FIG. 2) for use in guiding the catheter 23 into desired positions within the patient. As best seen in FIGS. 1 and 2, a suitable slide actuator 41 is mounted on the handle 25 for sliding movement longitudinally of the handle and is operatively connected to the deflectable segment of the catheter shaft 29 for movement between a first or neutral position (FIG. 1) corresponding to the undeflected configuration of the catheter shaft and a second (e.g., extended) position (FIG. 2) corresponding to the deflected configuration of the catheter shaft. The slide actuator 41 permits the catheter shaft 29 to be selectively deflected to any number of angular positions between the undeflected configuration and a predetermined maximum deflection (e.g., angular position) of the catheter. It is understood that any other suitable actuator (e.g., rotating, push button, lever, etc.) may be used to selectively adjust (e.g., deflect) the catheter shaft 29 without departing from the scope of this disclosure.

Another control line, such as a suitable cable or pull wire 43 (FIG. 4), extends from the segment of the catheter shaft 29 that is deflectable (e.g., the front end 35 of the illustrated catheter shaft) within the hollow catheter shaft and into the handle 25 and operatively connects the slide actuator 41 with the deflectable segment of the catheter via a pinion member 401 (FIG. 4 and described in further detail later herein) to which the pull wire is connected. While in the illustrated embodiment a single pull wire 43 is used to selectively deflect the catheter shaft 29, it is contemplated that two or more wires, cables or other suitable control lines may be used for selectively bending the catheter. It is also understood that the control line 43 may be any suitable control line other than a pull wire, such as a cable, string, tie, compression member or other suitable line useful to operatively connect the deflectable segment of the catheter shaft 29 to the pinion member 401 and hence the handle 25. The control line 43 associated with deflection of the catheter shaft 29 is different from the control line 39 associated with selectively configuring the electrode basket 33 to permit configuration of the electrode basket at least in part independent of the deflection of the catheter.

A conductive wire, or more particularly in the illustrated embodiment a twisted bundle 45 of two or more conductive wires (FIG. 4) corresponding to the multiple electrodes of the electrode basket 33, extends from the electrode basket within the catheter shaft 29 and into the handle 25 for electrical connection with the conductor assembly 27 to provide electrical communication between the power supply and the electrode basket. It is understood that the power supply may be any power supply, such as ultrasonic, RF or other suitable power supply.

Figure 4:
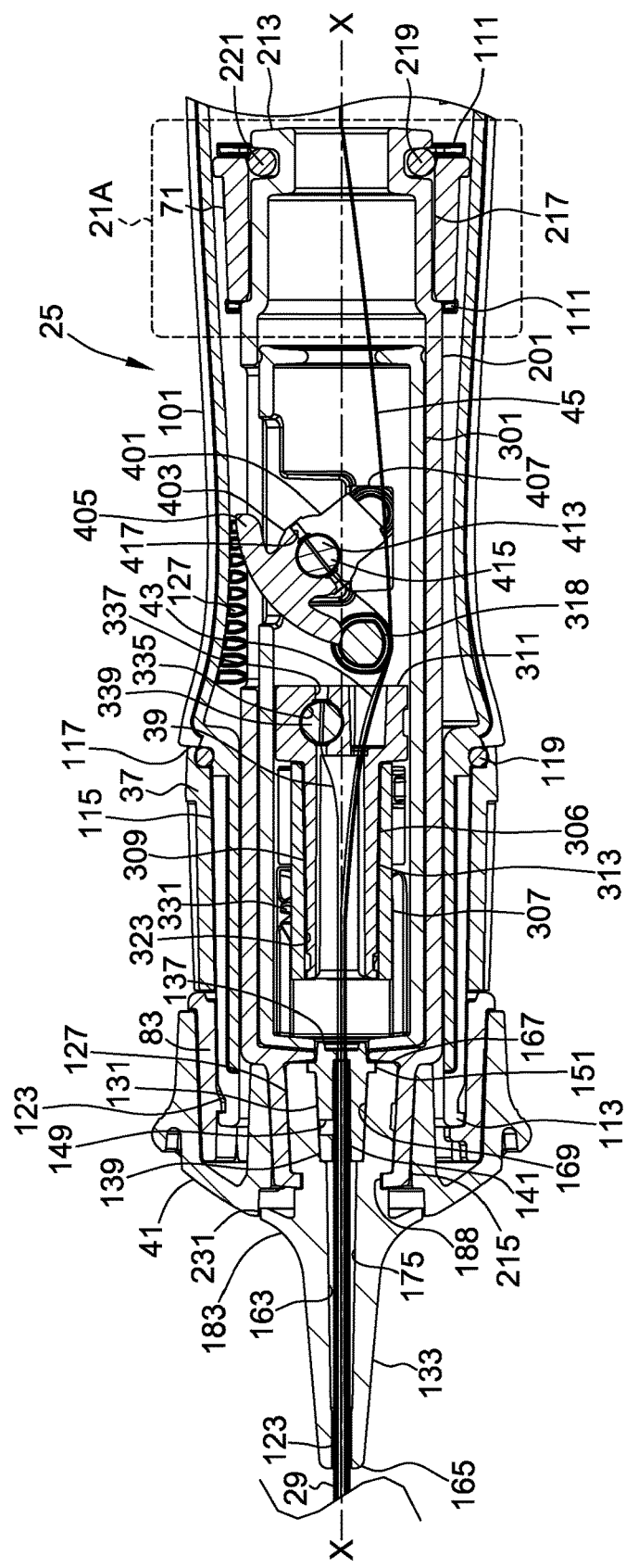
FIG. 4 is a cross-section of a portion of the handle of the catheter system of FIG. 1.
Figure 5:
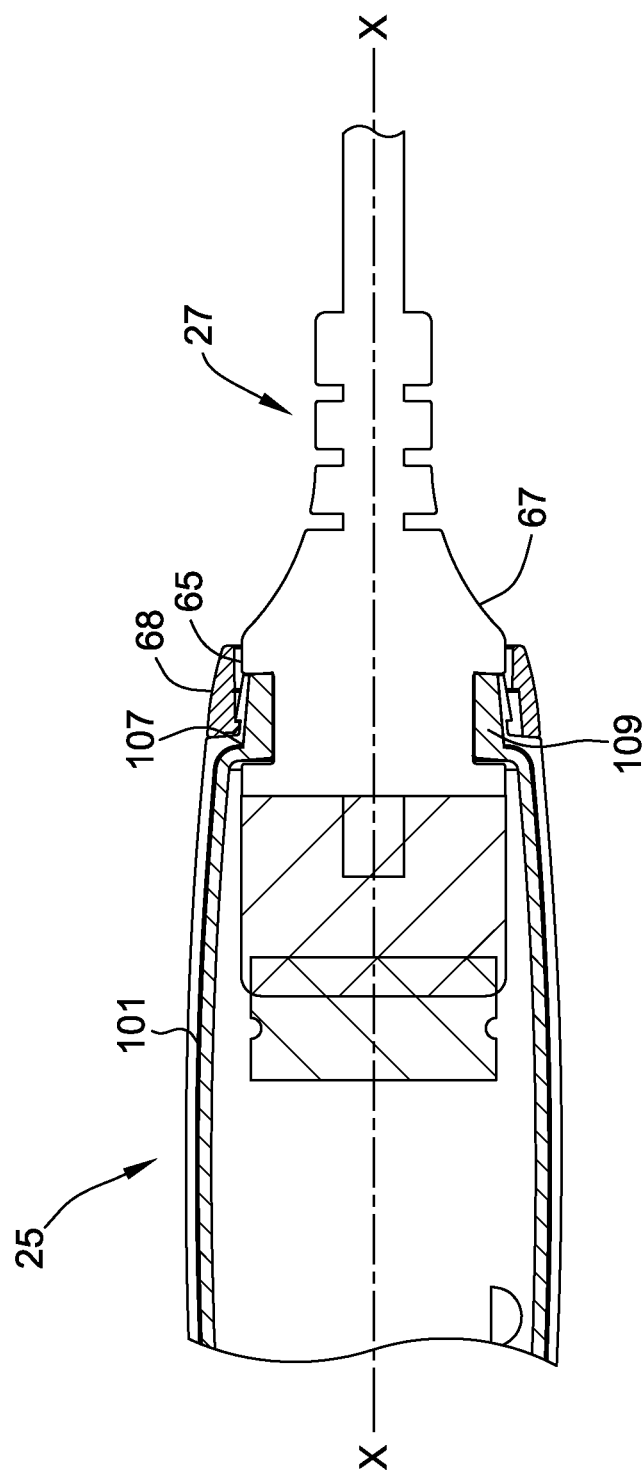
FIG. 5 is a cross-section of another portion of the handle of the catheter system of FIG. 1.
Figure 6:
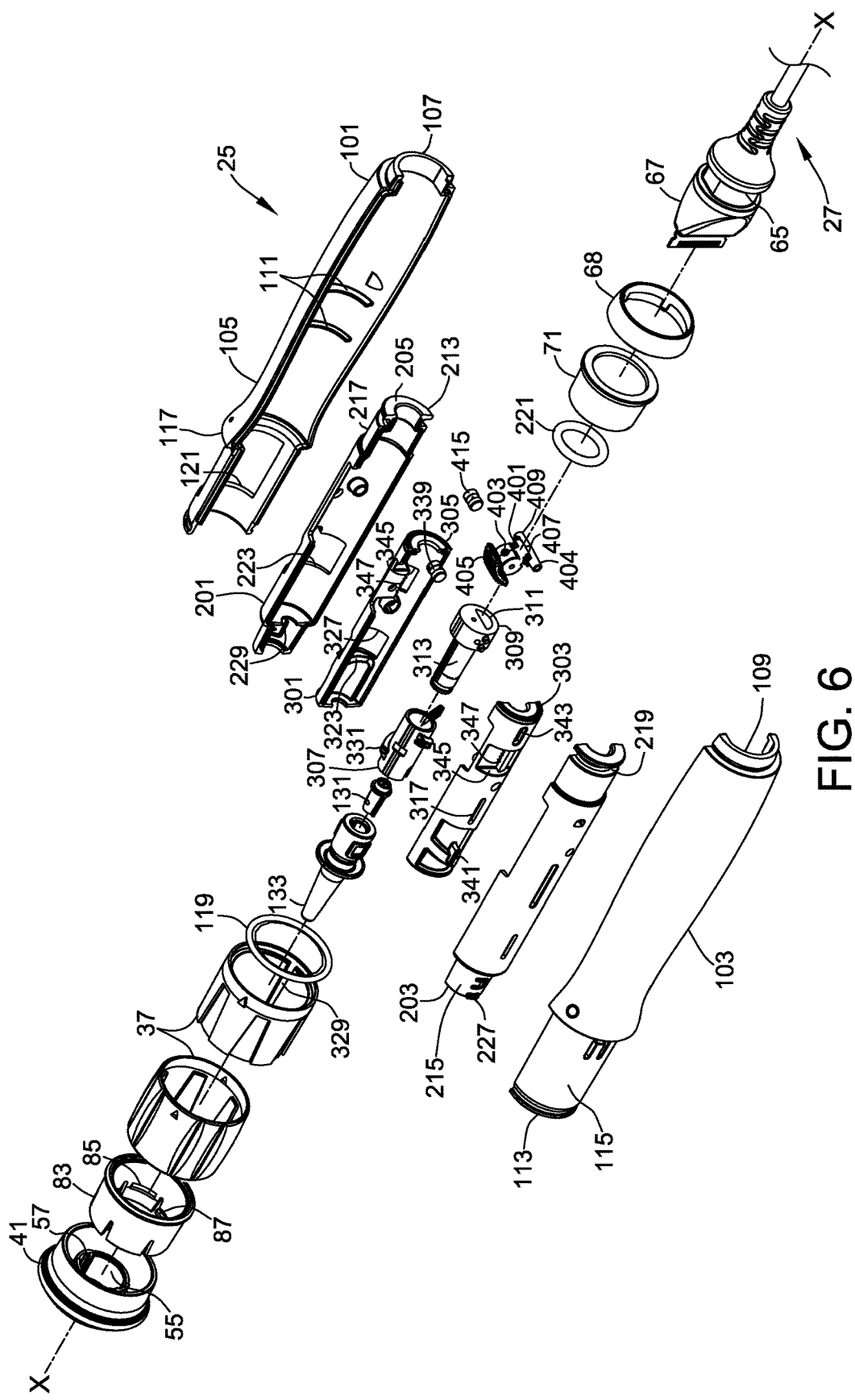
FIG. 6 is an exploded view of the handle of the catheter system of FIG. 1.

With particular reference now to FIGS. 4-6, the handle 25 has a longitudinal or lengthwise axis X and generally comprises an outermost housing, referred to herein as a handle housing 101, an intermediate housing, referred to herein as a barrel housing 201 extending longitudinally within the handle housing and being slidable longitudinally relative to the handle housing to broadly define an outer shuttle, and an innermost housing, referred to herein as a worm gear housing 301 extending longitudinally within the barrel housing and being slidable longitudinally relative to both the barrel housing and the handle housing to broadly define an inner shuttle. The illustrated handle housing 101 is of two piece construction (e.g., what is referred to herein as a top half 103 and a bottom half 105 of the handle housing). However, the handle housing 101 may be of any suitable alternative construction, such as of a single-piece construction or of more than two pieces.

The handle housing 101 has a proximal or rear end 107 (FIG. 5) to which the conductor assembly 27 is connected in any suitable manner. In the illustrated embodiment of FIG. 5, for example, connection is by an inward tapered collar 109 at the rear end 107 of the handle housing 101 seating within an annular channel 65 formed in a connection plug 67 of the conductor assembly 27. A retaining ring 68 seats over the tapered collar 109 to generally close the rear end 107 of the handle housing 101. As seen in FIGS. 4 and 6, the handle housing 101 includes a pair of internal arcuate ribs 111 extending radially inward from the inner surface of the handle housing. These ribs 111 extend circumferentially about the inner surface of the handle housing 101 to longitudinally locate and retain a slide bearing 71 within the handle housing.

Figure 18:
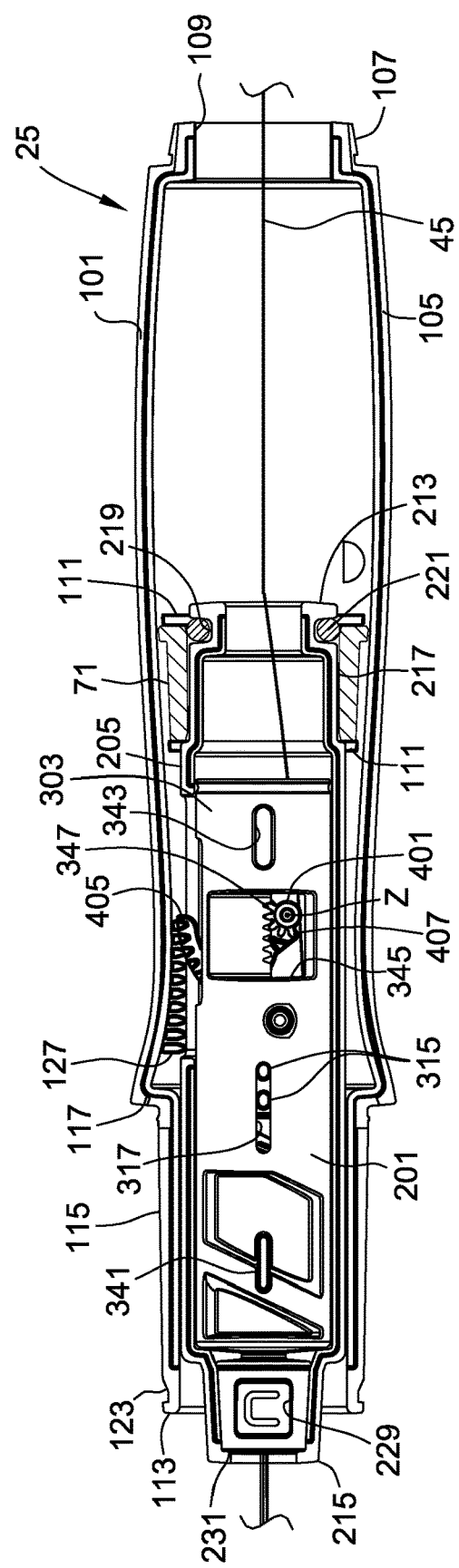
FIG. 18 is a top plan view of a bottom half of the handle housing, with a bottom half of the barrel housing and the entire worm gear housing and related internal components disposed therein.
Figure 19:
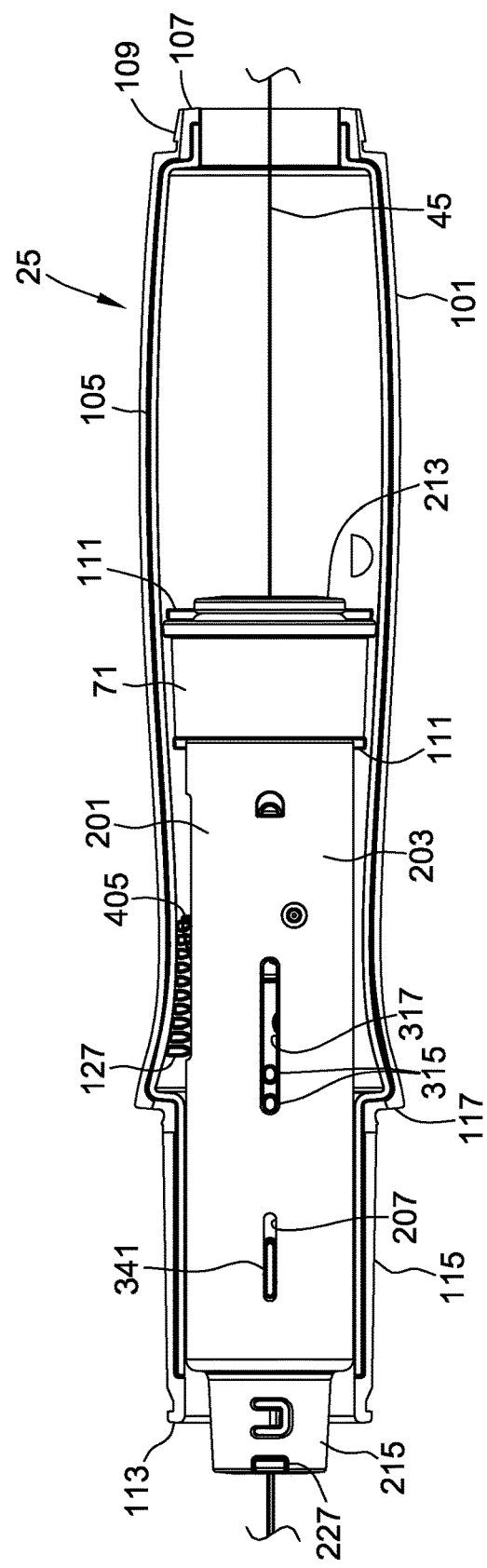
FIG. 19 is a top plan view of the bottom half of the handle housing, with the entire barrel housing, worm gear housing and related internal components disposed therein.
Figure 20:
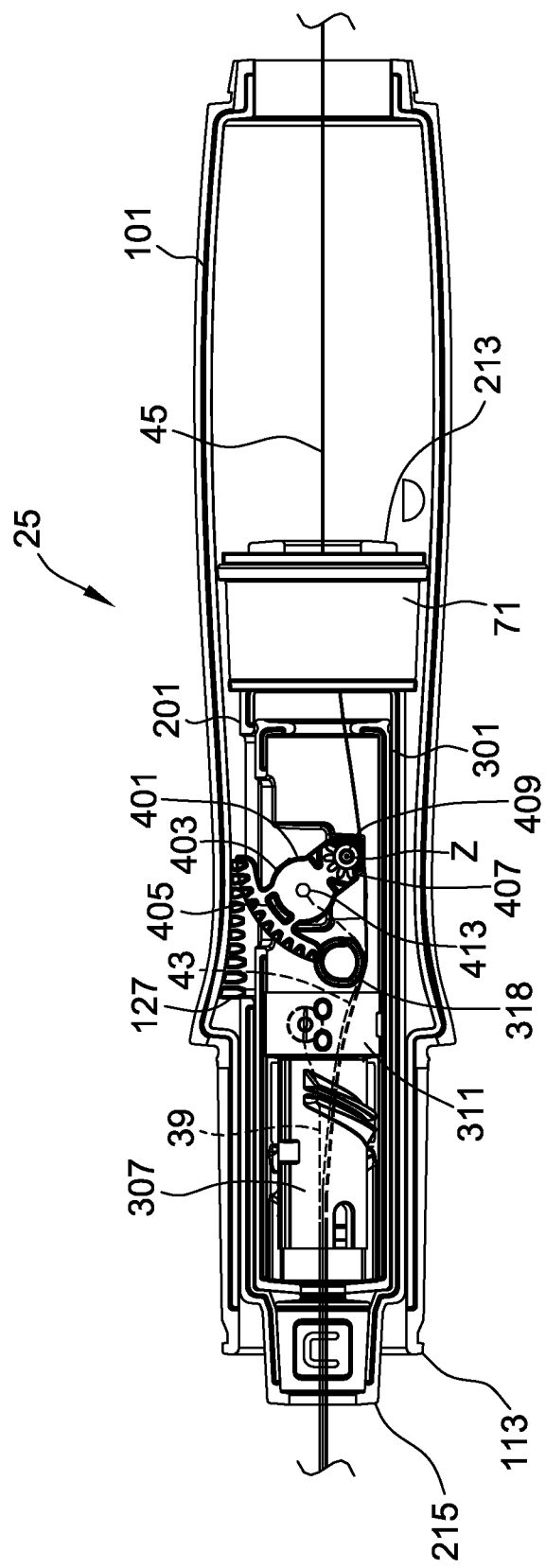
FIG. 20 is a top plan view of the bottom half of the handle housing, with the bottom half of the barrel housing, the bottom half of the worm gear housing, the worm gear assembly and the pinion member disposed therein, the pinion member being in an initial or neutral position corresponding to an undeflected configuration (FIG. 1) of the catheter shaft.

The handle housing 101 is configured adjacent its front end 113 as a cylindrical mount 115 for rotatably mounting the annular actuator 37 on the handle housing. A shoulder 117 (FIGS. 4 and 18) is formed in the outer surface of the mount 115 to function as a stop to facilitate longitudinal positioning of the annular actuator 37 on the handle housing 101. The shoulder 117 also accommodates a suitable sealing ring 119 (e.g., an elastomeric gasket or O-ring; FIGS. 4 and 6) to seal the interface between the annular actuator 37 and the handle housing 101. An opening 121 (FIG. 6) is formed in the bottom half 105 of the handle housing 101 at the cylindrical mount 115 to facilitate operative connection of the annular actuator 37 with the electrode basket 33 via the worm gear assembly 306 as described in detail later herein.

Figure 7:
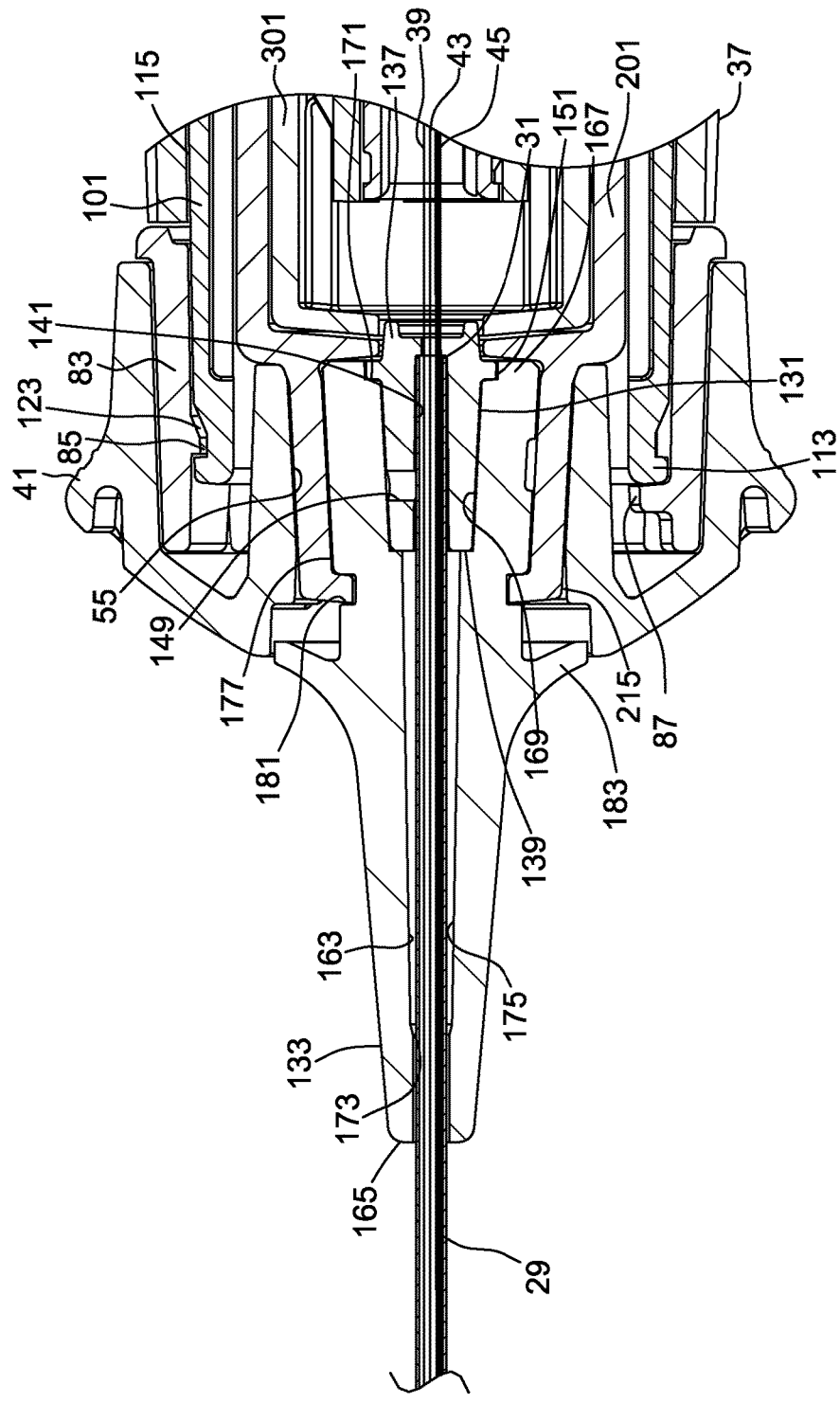
FIG. 7 is an enlarged portion of the cross-section of FIG. 4.
Figure 8:
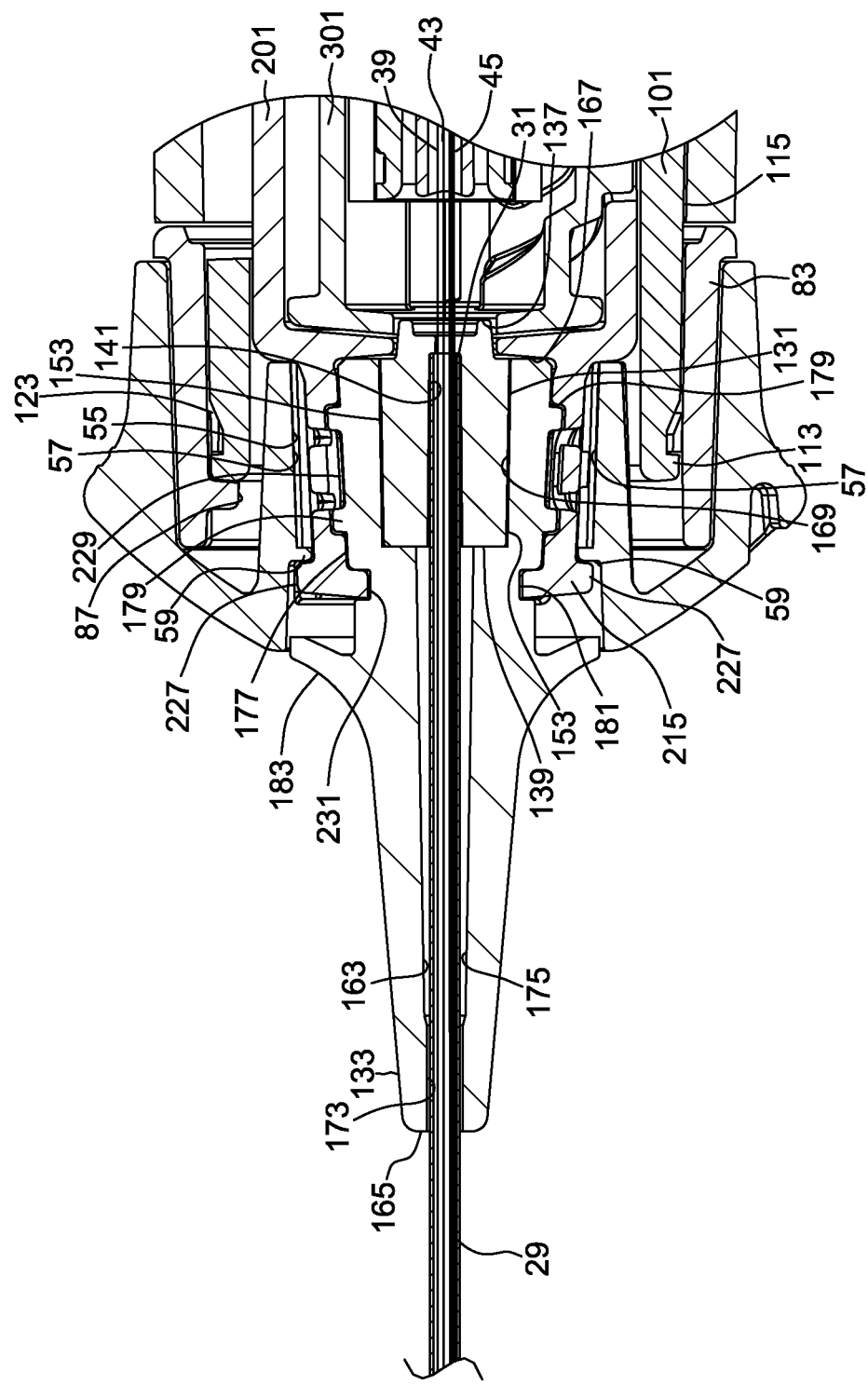
FIG. 8 is a cross-section of the handle taken perpendicular to the cross-section of FIG. 7.

An annular groove 123 is formed in the outer surface of the handle housing 101 to facilitate mounting a sleeve 83 on the front end 113 of the handle housing. The sleeve 83, as illustrated in FIGS. 4 and 6-8, has a first set of internal projections 85 (FIGS. 6 and 7) extending radially inward from the inner surface of the sleeve. These projections 85 seat within the annular groove 123 to mount the sleeve 83 on the handle housing 101. A second set of internal projections 87 (one of which is illustrated in FIG. 7 and the other in FIG. 8) extends radially inward from the inner surface of the sleeve 83 in longitudinally spaced relationship with the first set of internal projections 85, and more particularly nearer to a front end of the sleeve. With the sleeve 83 mounted on the handle housing 101, the second set of internal projections 87 abuts against the front end 113 of the handle housing as illustrated in FIGS. 4, 7 and 8 to secure the sleeve on the handle housing against longitudinal movement relative thereto.

Referring now to FIGS. 9-12, the illustrated worm gear housing 301 (broadly, the inner shuttle of the handle 25) is of two-piece construction, referenced herein as a top half 303 and a bottom half 305. In other suitable embodiments the worm gear housing 301 may be of single-piece construction, or constructed of more than two pieces. The worm gear assembly 306 (FIGS. 9 and 12) is positionable longitudinally within the worm gear housing 301 and includes a worm gear 307 rotatable on a linear bushing 309. The linear bushing 309 has a head 311, and a smaller diameter shaft 313 extending longitudinally forward from the head. A pair of locating pins 315 project from the outer circumference of the head 311 for seating in a longitudinally extending slot 317

(as illustrated best in FIG. 9) in the top half 303 of the worm gear housing 301 to locate and retain the worm gear assembly 306 in the worm gear housing and to inhibit the head 311 of the worm gear bushing 309 against rotation relative to the worm gear housing. The slot 317 is sized in length to permit longitudinal translation of the worm gear assembly 306 relative to the worm gear housing 301 in response to rotation of the worm gear 307 on the bushing 309. A distal or front end 319 of the bushing shaft 313 has an annular groove 321 formed therein to facilitate mounting of the worm gear 307 on the bushing 309.

Figure 10:
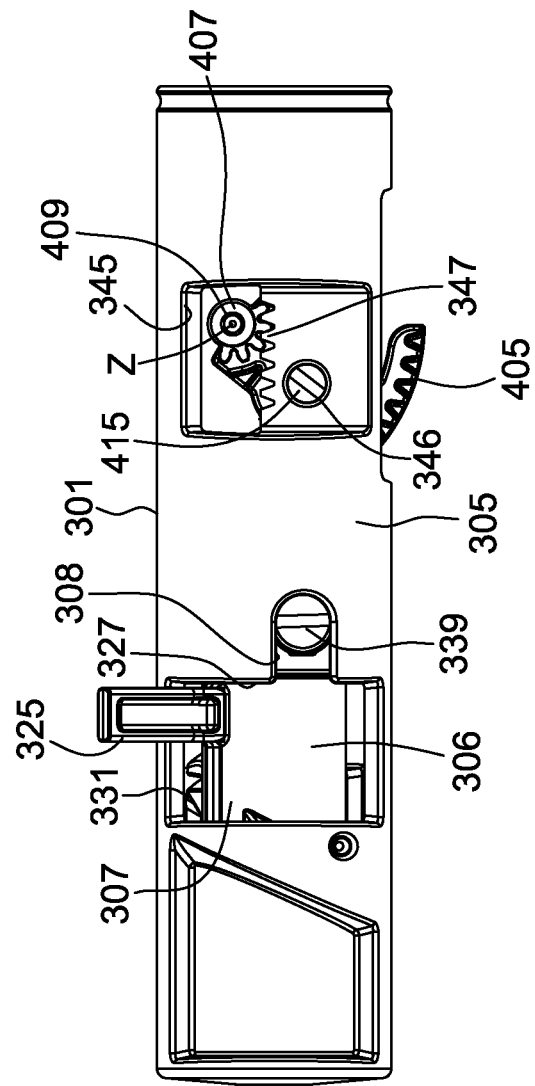
FIG. 10 is a bottom plan view of the assembled worm gear housing, worm gear assembly and pinion member.

The illustrated worm gear 307 is generally tubular, having a central channel 323 for receiving the bushing shaft 313 therein. Catches (not shown) project radially inward of the channel 323 from the inner surface of the worm gear 307 for seating in the annular groove 321 of the bushing shaft 313 to mount the worm gear on the bushing for rotation on the shaft of the bushing. A lever arm 325 extends radially outward from the worm gear 307 for operative connection with the annular actuator 37. In particular, the bottom half 305 of the worm gear housing 301 has a window 327 (FIGS. 6, 10 and 11) through which the worm gear lever arm 325 extends when the worm gear assembly 306 is otherwise housed within the worm gear housing as illustrated in FIG. 10. A longitudinally extending groove 329 (FIG. 6) is formed in the inner surface of the annular actuator 37 and is configured to receive the outer end of the worm gear lever arm 325 upon assembly of the handle 25 such that rotation of the annular actuator drives rotation of the worm gear 307 relative to the worm gear housing 301 (and hence the handle 25).

Figure 11:
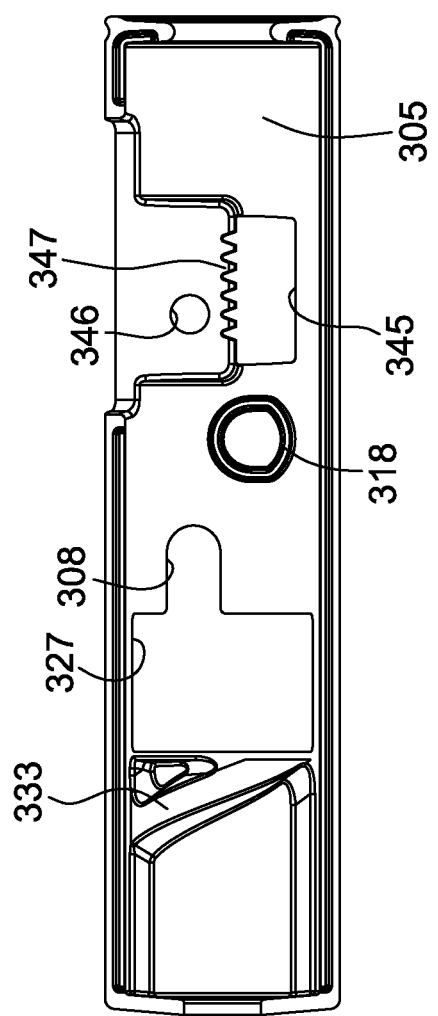
FIG. 11 is a top plan view of a bottom half of the worm gear housing.
Figure 12:
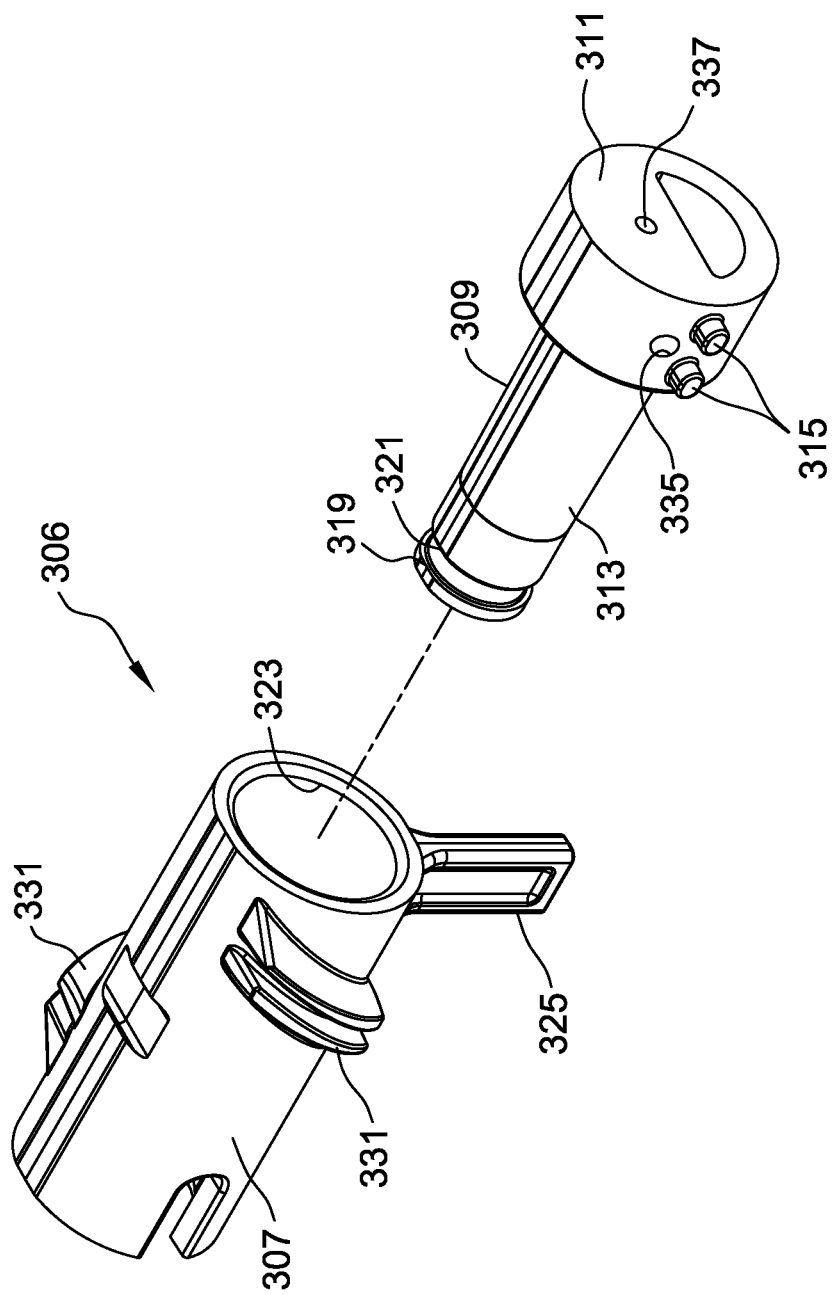
FIG. 12 is an exploded perspective view of a worm gear assembly of the handle of the catheter system of FIG. 1.

Suitable worm gear threads 331 project outward from the worm gear 301 (e.g., two sets of worm gear threads are illustrated in the various embodiments, such as in FIG. 12) and seat within corresponding guide channels 333 (one of which is illustrated in FIG. 11) formed in the respective inner surfaces of the top half 303 and bottom half 305 of the worm gear housing 301. The worm gear threads 331 and corresponding guide channels 333 are configured such that upon rotation of the worm gear 307 relative to the worm gear housing 301 (e.g., due to rotation of the annular actuator 37 from an initial or neutral position corresponding to the collapsed configuration of the electrode basket 33 to a rotated position corresponding to the expanded configuration of the electrode basket), the worm gear assembly 306 moves linearly (i.e., longitudinally) rearward relative to the worm gear housing.

As best seen in FIG. 4, the shaft 313 of the linear bushing 309 is hollow. A threaded bore 335 extends transversely through the sidewall of the bushing head 311, with a substantially smaller bore 337 being formed longitudinally in the head of the bushing so as to provide communication between the hollow shaft 313 of the bushing 309 and the threaded bore formed in the head of the bushing. In this manner, the pull wire 39 associated with the electrode basket 33 extends into the worm gear housing 301 and through the worm gear 307 and bushing shaft 313. The pull wire 39 further extends through the smaller bore 337 in the head 311 of the bushing 309 into the threaded bore 335. A suitable fastener or rotatable plug 339 is disposed in the threaded bore 335 and captures (e.g., coils) the pull wire 39 to operatively connect the electrode basket 33 with the worm gear assembly 306, and hence the annular actuator 37 via the lever arm 325. The plug 339 also facilitates predetermined tensioning of the pull wire 39, e.g., upon assembly or subsequent adjustment of the handle. A notch 308 (FIG. 10) is formed in the bottom half 305 of the worm gear housing 301 to provide access to the plug 339 even after assembly of the worm gear housing and barrel housing 201.

In operation, rotation of the annular actuator 37 from its initial position to its rotated position causes the worm gear assembly 306 to translate longitudinally rearward relative to the worm gear housing 301, thus further tensioning the pull wire 39 (i.e., broadly, acting on the control line) to effect expansion of the electrode basket 33 as illustrated in FIG. 3. Rotation of the annular actuator 37 in the opposite direction releases the additional tension in the pull wire 39 to thereby allow the electrode basket 33 to return to its collapsed configuration (FIG. 1).

Figure 15:
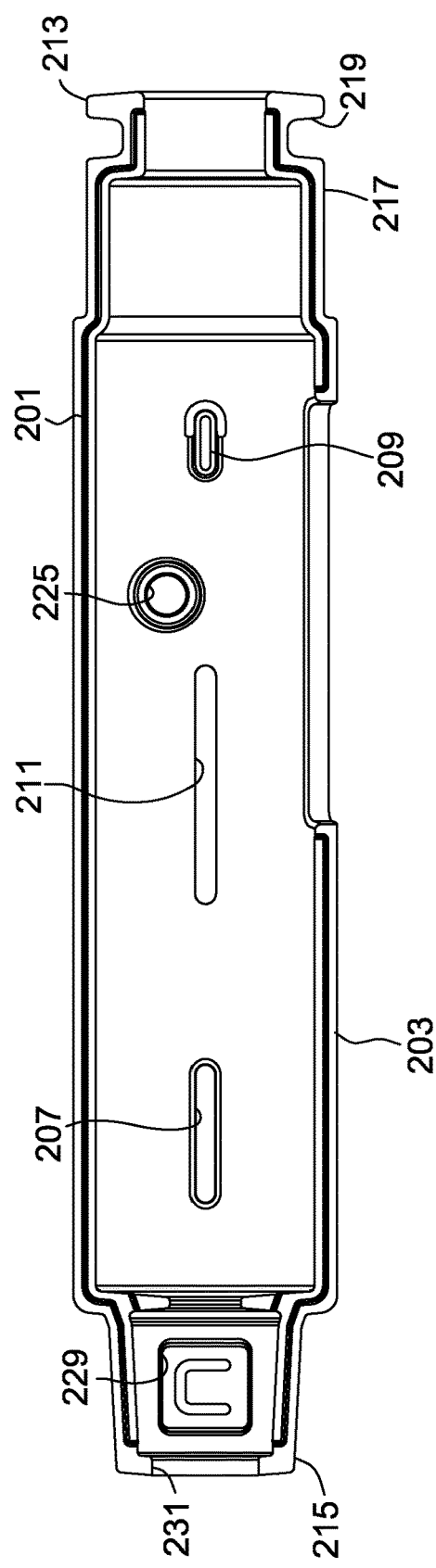
FIG. 15 is a bottom plan view of a top half of a barrel housing of the handle.
Figure 16:
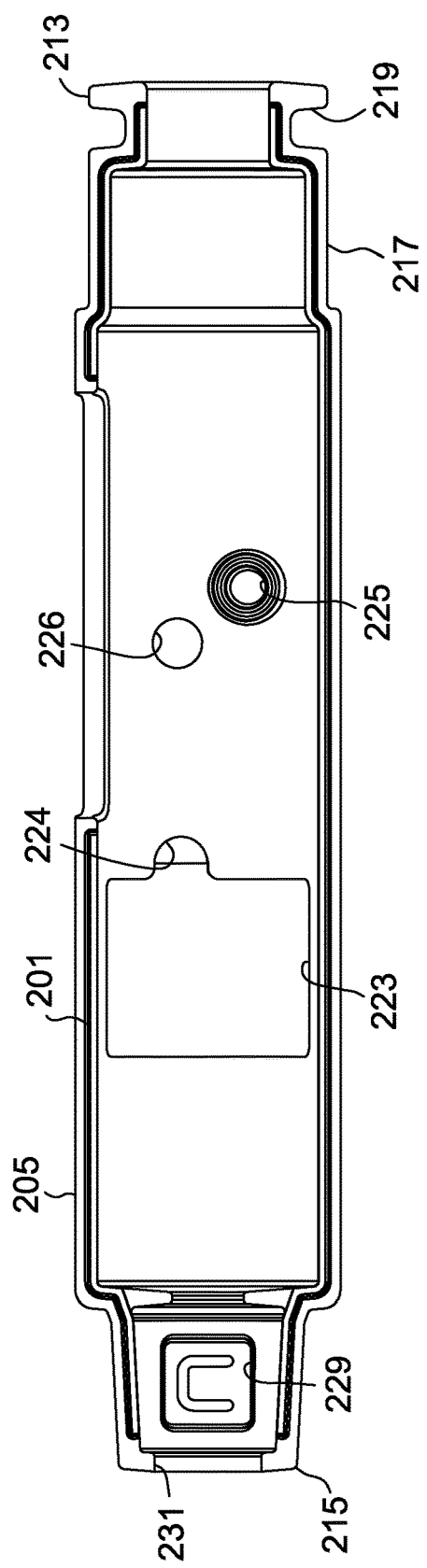
FIG. 16 is a top plan view of a bottom half of the barrel housing of the handle.

With general reference now to FIGS. 4, 6 and 15-21, the barrel housing 201 (broadly, the outer shuttle) is also of two-piece construction, including what is referred to herein as a top half 203 (FIG. 15) and a bottom half 205 (FIG. 16). In other suitable embodiments, the barrel housing 201 may be of single-piece construction, or constructed of more than two pieces. The top half 203 of the barrel housing 201, as best illustrated in FIG. 15, includes a guide slot 207 for receiving a locating tab 341 (FIGS. 6, 9 and 9A) that projects radially outward from the outer surface of the top half 303 of the worm gear housing 301. This guide slot 207 is sized in length to accommodate sliding movement of the locating tab 341—and hence the worm gear housing 301—relative to the barrel housing 201. A second locating tab 209 (FIG. 15) extends radially inward from the inner surface of the top half 203 of the barrel housing 201—in longitudinally spaced relationship with the guide slot 207—and is receivable in a corresponding slot 343 (FIGS. 6 and 9) in the top half 303 of the worm gear housing 301. A third locating tab (not shown) extends radially inward from the inner surface of the top half 103 of the handle housing 101 and is receivable in a corresponding slot 211 (FIGS. 6 and 15) in the top half 203 of the barrel housing 201. Locating the various tabs 341, 209 (the third tab, projecting from the handle housing 101, not being shown) within the corresponding slots 207, 343, 211 in this manner also inhibits relative rotation of the respective housings 301, 201, 101 following assembly of the handle 25.

The illustrated barrel housing 201 has a longitudinally proximal or rear end 213, and a distal or front end 215. As seen best in FIGS. 17, 18 and 21A, a segment 217 of the barrel housing 201 adjacent its rear end 213 is sized in cross-section (e.g., in diameter in the illustrated embodiment) for slidable disposition within the slide bearing 71 to centrally position the barrel housing within the handle housing 101 while permitting sliding movement of the barrel housing (i.e., the outer shuttle) relative to the handle housing. An annular groove 219 is formed in the barrel housing segment 217 for seating an elastomeric sealing ring 221, such as an O-ring or other suitable sealing ring. The sealing ring 221 outer diameter is sized for sliding contact of the sealing ring with the inner surface of the slide bearing 71 upon sliding movement of the barrel housing 201 relative to the handle housing 101.

In a more particular embodiment, the elastomeric sealing ring 221 is generally loosely retained within the annular groove 219 of the barrel housing 201. Upon assembly of the barrel housing 201 and sealing ring 221 into the handle housing 101 (and hence in the slide bearing 71), the radially outer surface of the sealing ring is compressed by the slide bearing to generate friction between the sealing ring and the slide bearing to facilitate retention of the barrel housing at generally any position along the possible longitudinal travel of the barrel housing relative to the handle housing. In one particularly suitable embodiment, the friction between the sealing ring 221 and slide bearing 71 is sufficient to retain the barrel housing 201 at a desired longitudinal position, but sufficiently loose enough to permit the operator of the catheter system 21 to move the barrel housing the slide actuator 41 (e.g., to deflect the catheter shaft 29) with one hand.

As one example, the elastomeric sealing ring 221 may be suitably constructed, and more suitably molded, of silicone. It is understood, though, that the sealing ring 221 may be constructed of another suitable elastomeric material or combination of materials without departing from the scope of this disclosure. The slide bearing 71 is suitably of single-piece molded plastic. For example, in one suitable embodiment the slide bearing 71 is constructed of an acetal material. In other embodiments, however, the slide bearing 71 may be made of other suitable materials or combination of materials.

Figure 21:
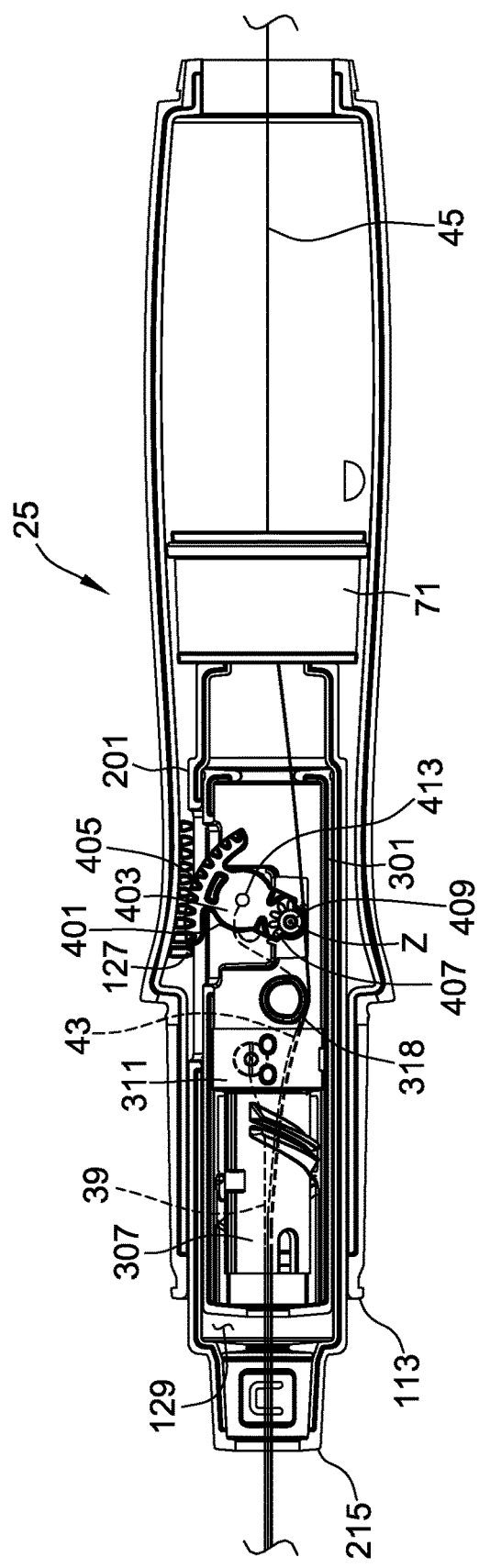
FIG. 21 is a top plan view similar to FIG. 20 with the pinion member pivoted relative to the handle housing to a maximum pivoted position corresponding to the maximum deflected configuration (FIG. 2) of the catheter shaft.
Figure 21A:
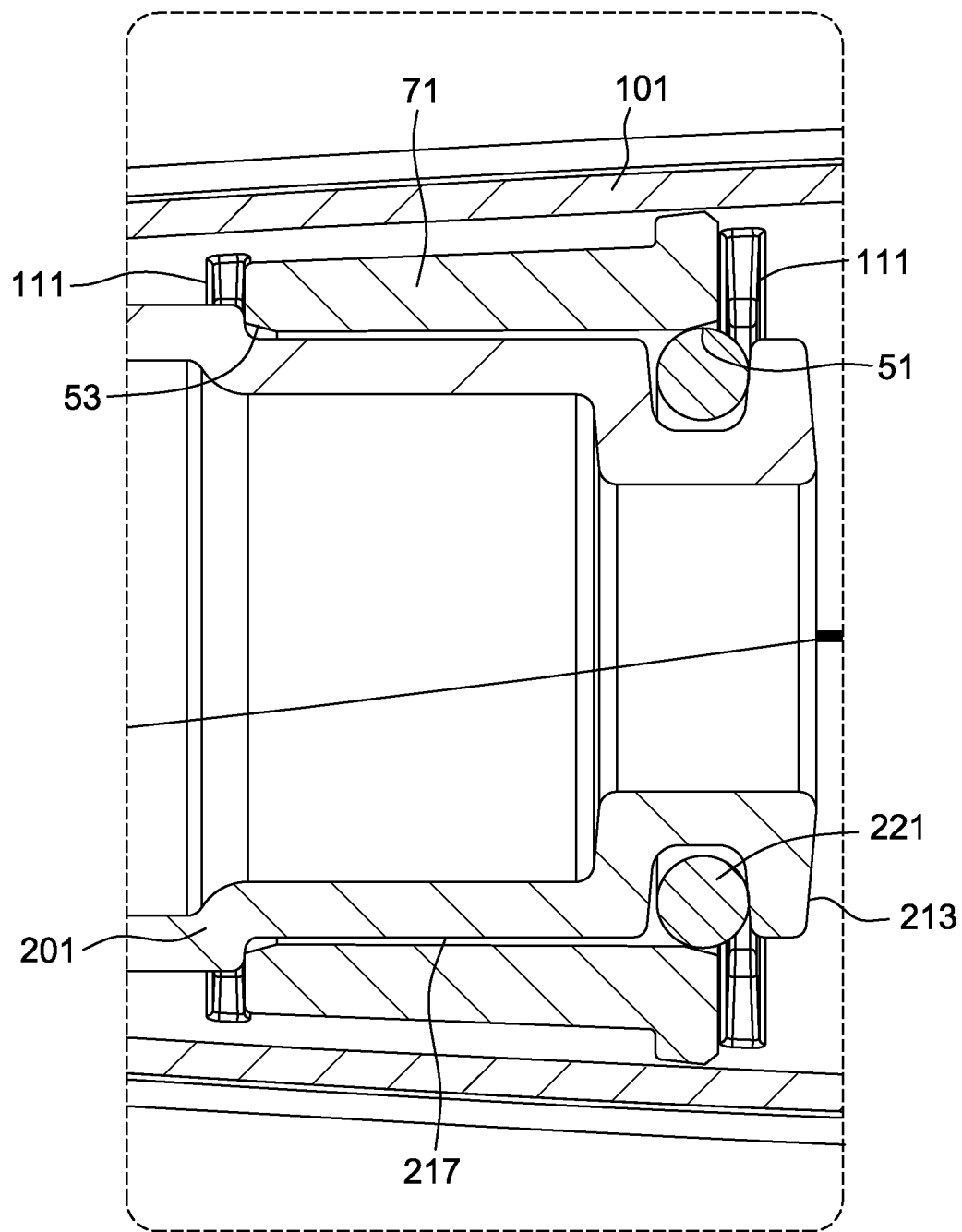
FIG. 21A is an enlarged cross-section of a portion of the handle of FIG. 4.

As illustrated in FIG. 21A, the inner surface (e.g., inner diameter) of the slide bearing 71 according to one embodiment is chamfered 51 at its longitudinal back end and defines a neutral or initial position of the barrel housing 201 (corresponding to the undeflected configuration of the catheter). The chamfer 51 provides compression relief of the sealing ring 221 in the neutral position of the barrel housing 201 to inhibit compression set over long periods of non-use of the catheter system 21. The inner surface of the illustrated slide bearing 71 is also chamfered 53 at its longitudinal front end to provide a detent at the maximum longitudinal travel of the barrel housing 201 to thereby provide feedback to the operator that the barrel housing is at the maximum longitudinal travel thereof.

Figure 17:
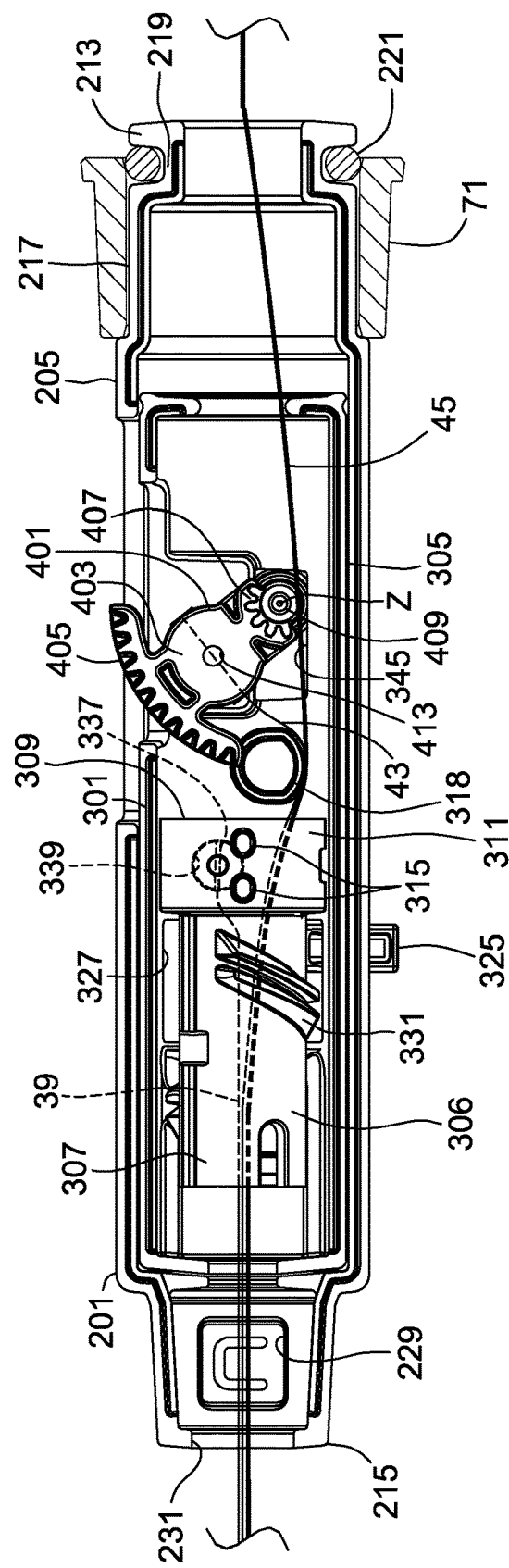
FIG. 17 is a top plan view of the bottom half of the barrel housing with the bottom half of the worm gear housing, the worm gear assembly and the pinion member disposed therein.

The bottom half 205 of the barrel housing 201 includes a window 223 (FIGS. 6 and 16) formed therein to accommodate passage of the worm gear lever arm 325 therethrough (see, e.g., FIG. 17). The window 223 includes a notch 224 (FIG. 16) that aligns with the notch 308 (FIG. 10) of the bottom half 305 of the worm gear housing 301 to provide access to the plug 339 for adjusting the tension in the pull wire 39 even after assembly of the worm gear housing and barrel housing 201.

The top half 203 and bottom half 205 of the barrel housing 201 also have respective, opposed pin seats 225 (FIGS. 15 and 16) extending generally transversely inward from the respective inner surfaces thereof. These pin seats 225 are configured to pivotally retain the pinion member 401 (FIG. 17) in the barrel housing 201 for longitudinal movement along with the barrel housing (i.e., the outer shuttle) relative to the handle housing 101.

Figure 13:
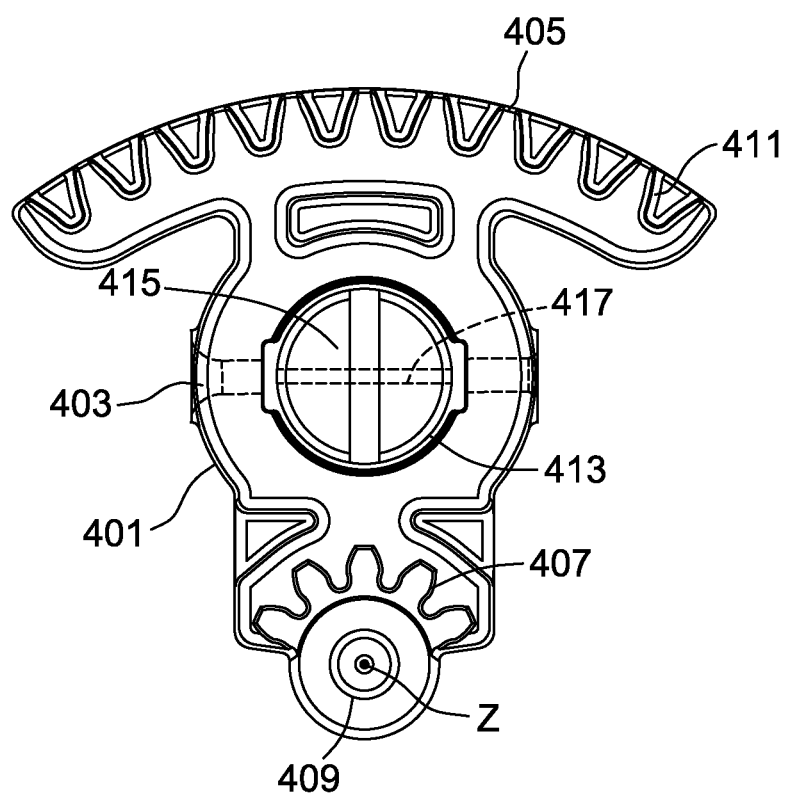
FIG. 13 is a top plan view of a pinion member of the handle.
Figure 14:
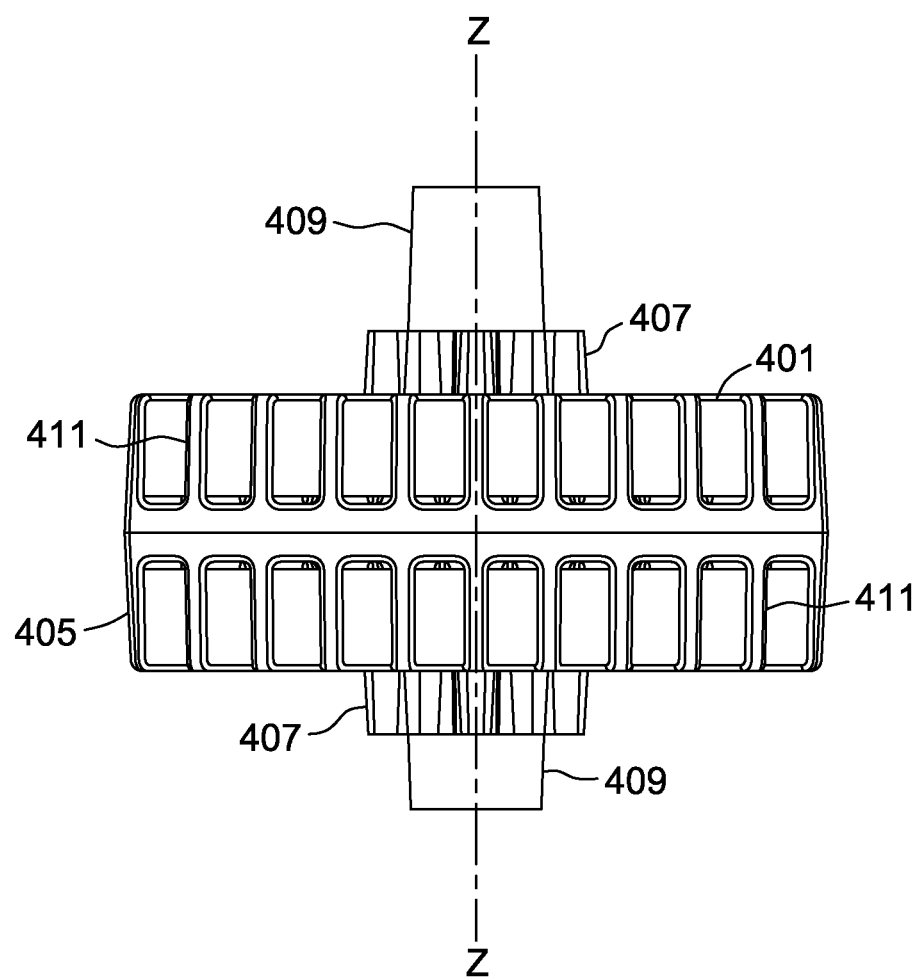
FIG. 14 is a front elevation of the pinion member of FIG. 13.

With particular reference to FIGS. 13 and 14, the pinion member 401 comprises a hub 403, a primary (broadly, a first) pinion gear 405 disposed on one transverse side of the hub, and a pair of secondary pinion gears 407 (broadly, a second or at least one second pinion gear) disposed on a transverse side of the hub opposite the primary pinion gear. A pin 409 extends outward from each of the respective secondary pinion gears 407 as illustrated in FIG. 14 to define a pivot or rotation axis Z of the pinion member 401. Upon assembly of the handle 25, the pins 409 seat within the respective pin seats 225 of the barrel housing 201 to pivotally secure the pinion member 401 in the barrel housing 201 while permitting pivoting movement of the pinion member relative to the barrel housing about the pivot axis Z.

As seen best in FIG. 14, the primary pinion gear 405 comprises two parallel rows of gear teeth 411. It is understood that in alternative embodiments the primary pinion gear 405 may comprise a single row of gear teeth extending the width of the primary pinion gear, or a single row of gear teeth extending less than the entire width of the primary pinion gear. In other alternative embodiments, the primary pinion gear 405 may comprise more than two rows of gear teeth. A respective corresponding rack 127 (one of which is illustrated in FIGS. 4 and 18-21, the other of which is not shown but is identical to that illustrated in these Figures) extends inward from the inner surface of each of the top half 103 and bottom half 105 of the handle housing 101. Accordingly, upon sliding movement of the barrel housing 201 (i.e., the outer shuttle) relative to the handle housing 101, the interengagement of the primary pinion gear teeth 411 with the corresponding racks 127 on the handle housing 101 cause the pinion member 401 to pivot relative to the barrel housing 201 about the pivot axis Z of the pinion member from an initial or neutral position (FIG. 20) toward a maximum pivoted position (FIG. 21).

A central bore 413 (FIG. 13) extends at least into, and in the illustrated embodiment it extends through (e.g., from the top to the bottom of), the hub 403 of the pinion member 401. The bore 413 is threaded and receives a suitable fastener or rotatable plug 415 therein. A substantially smaller bore 417 extends transversely through the side of the pinion member hub 403 into open communication with the central bore 413. As illustrated in FIGS. 4 and 17, the pull wire 43 associated with deflection of the catheter shaft 29 extends into the handle housing 101, into the barrel housing 201 (and worm gear housing 301), and then through the smaller bore 417 in the hub 403 of the pinion member 401 into the central bore 413. The plug 415 is used to coil the pull wire 43 to thereby selectively tension the pull wire to a predetermined desired tension. Accordingly, the catheter shaft 29 is operatively connected to the barrel housing 201 (i.e., the outer shuttle) via the pinion member 401.

Figure 9:
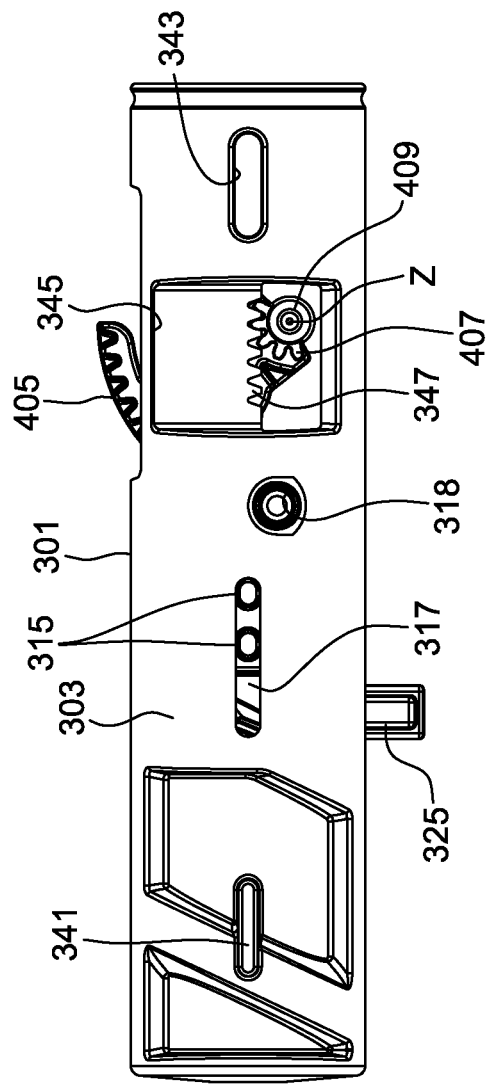
FIG. 9 is a top plan view of an assembled worm gear housing, worm gear assembly and pinion member.
Figure 9A:
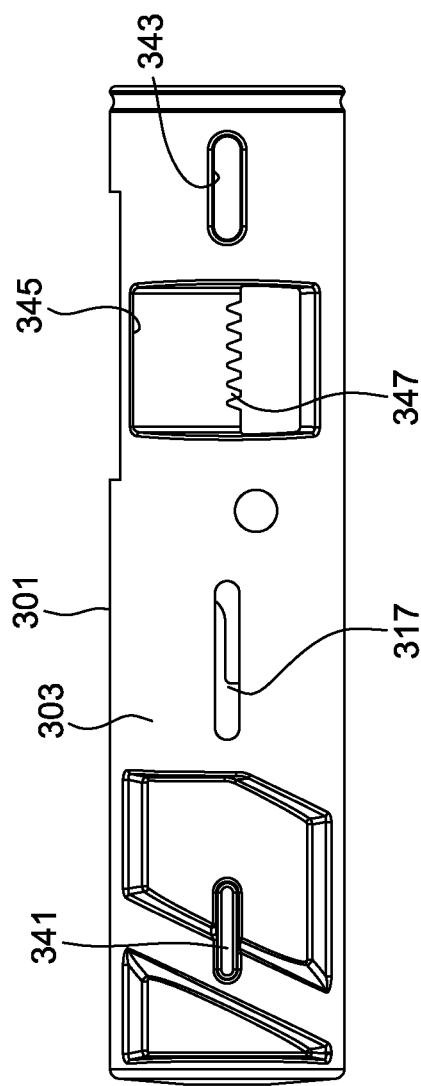
FIG. 9A is a top plan view of the worm gear housing.
Figure 10A:
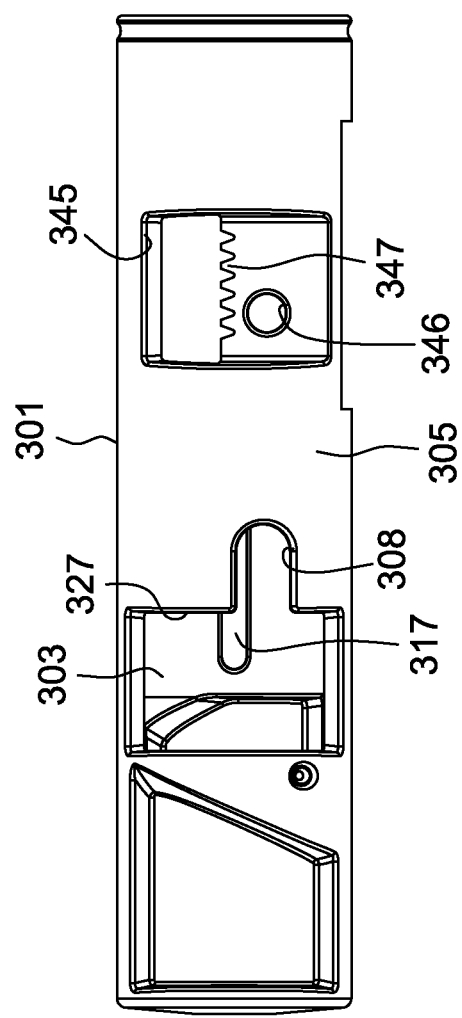
FIG. 10A is a bottom plan view of the worm gear housing.

As illustrated in FIGS. 9 and 10, the pinion member 401 is disposed in part within the worm gear housing 301 upon assembly of the worm gear housing, with the pins 409 extending outward from windows 345 formed in the worm gear housing such that pins can seat in the respective pin seats 225 of the barrel housing 201. An opening 346 (FIGS. 10 and 10A) in the bottom half 305 of the worm gear housing 301 and corresponding opening 226 (FIG. 16) in the bottom half 205 of the barrel housing 201 provide access to the plug 415 (see, e.g., FIG. 10) to permit adjustment of the tension of the pull wire 43 even after assembly of the worm gear housing and barrel housing.

The central bore 413 of the pinion member 401 is offset from the pins 409 (and hence the pivot axis Z) such that upon pivoting movement of the pinion member about its pivot axis, the central bore 413 and plug 415 to which the pull wire 43 is connected orbits about the pivot axis of the pinion member. More particularly, in the initial or neutral position (FIGS. 17-20) of the pinion member 401 corresponding to the undeflected configuration of the catheter shaft 29, the primary pinion gear 405 and hence the central bore 413 and plug 415 of the pinion member are at a more longitudinally forward position relative to the barrel housing 201. In particular, as illustrated best in FIGS. 17 and 20, to facilitate proper alignment of the pinion member 401 in its neutral position a post 318 extends within the worm gear housing 301 between the opposed top half 303 and bottom half 305 of the worm gear housing. In the neutral position of the pinion member 401, the primary pinion gear 405 abuts against the post, with the rearwardmost teeth of the primary pinion gear intermeshed with the rearwardmost teeth of the rack 127 of the housing 101.

Upon sliding movement of the barrel housing (i.e., the outer shuttle) in a forward direction relative to the handle housing 101, the interengagement between the primary pinion gear teeth 411 and the racks 127 on the handle housing cause the pinion member to pivot about its pivot axis Z such that the primary pinion gear and hence the central bore 413 and plug 415 move in a generally rearward direction relative to the barrel housing 201 as illustrated in FIG. 21. Because the catheter shaft 29 (to which the pull wire 43 is connected) is being moved longitudinally forward along with the barrel housing 201 but the plug 415 (to which the pull wire 43 is also connected) is pivoted rearward relative to the barrel housing, tension in the pull wire 43 increases and thus causes the deflectable segment of the catheter shaft 29 to deflect towards its maximum deflected configuration. Rearward movement of the barrel housing 201 causes the pinion member 401 to pivot back toward its neutral position, thus releasing the additional tension in the pull wire 43 to allow configuration of the catheter shaft 29 back toward its undeflected configuration.

The front end 215 of the barrel housing 201 includes a pair of detents 227 (FIG. 8) extending radially outward from the housing. The slide actuator 41, as illustrated in FIGS. 6-8, has a central opening 55 sized for receiving the front end 215 of the barrel housing 201 therein. A pair of opposed guide channels 57 (FIG. 8) extend longitudinally in the inner surface of the slide actuator 41 to accommodate the outward extending detents 227 of the barrel housing 201. A pair of shoulders 59 (FIG. 8) are formed on the inner surface of the slide actuator 41 adjacent the longitudinally front end thereof.

To operatively connect the slide actuator 41 to the barrel housing 201 (i.e., the outer shuttle), the slide actuator is placed on the front end 215 of the barrel housing, with the detents 227 of the barrel housing disposed in and sliding along the channels 57 in the inner surface of the slide actuator. Upon further placement of the slide actuator 41 onto the barrel housing 201, the detents 227 become positioned just forward of the shoulders 59 formed in the inner surface of the slide actuator. The slide actuator 41 is then rotated relative to the barrel housing 201 so that the detents 227 seat on the shoulders 59 of the slide actuator to interlock and hence operatively connect the slide actuator to the barrel housing 201. In this manner, sliding movement of the slide actuator 41 relative to the handle housing 101 as illustrated in FIG. 2 operatively slides the barrel housing (i.e., the outer shuttle) therewith, and hence pivots the pinion member 401 relative to the barrel housing to selectively configure the catheter between its undeflected and deflected configurations. It is understood that an outer shuttle may be configured other than as a housing such as the barrel housing 201 without departing from the scope of this disclosure, as long as the pull wire 43 (i.e., the control wire) associated with deflection of the catheter is operatively coupled with the outer shuttle such that movement of the outer shuttle relative to the handle acts on the catheter shaft 29, i.e., deflects the catheter shaft.

The catheter system 21 thus allows deflection of the catheter shaft 29 independent of selective configuration of the electrode basket 33 between its collapsed and expanded configurations using the annular actuator 37. However, because the worm gear housing 301 and worm gear assembly 306 (to which the electrode basket pull wire 39 is connected) are disposed within and carried by the barrel housing 201, the worm gear assembly and hence the connection point at which the electrode basket pull wire 39 is connected to the handle 25 move longitudinally forward relative to the handle housing 101 along with the barrel housing in response to actuation of the slide actuator 41. As a result, regardless of whether the electrode basket 33 is in its collapsed configuration or its expanded configuration, the length of the pull wire 39 from the electrode basket to the connection point on the worm gear assembly 306 is relatively shortened in response to actuation of the slide actuator 41 to deflect the catheter shaft 29. Accordingly, absent compensation for this shift, the pull wire 39 associated with the electrode basket 33 is susceptible to decreased tension and even the possibility of slack in the pull wire upon deflection of the catheter shaft 29. To this end, according to one embodiment herein the pull wire 39 associated with the electrode basket 33 is responsive to adjustment of the catheter shaft 29 configuration to thereby inhibit slack from forming in the electrode basket pull wire.

More particularly, in the illustrated embodiment the worm gear housing 301—disposed within the barrel housing 201 and together with the worm gear assembly defining an inner shuttle of the handle 25—includes a rack 347 (FIGS. 9, 9A, 10 and 10A) formed along respective edges of the windows 345 formed in top half 303 and bottom half 305 of the worm gear housing 301. As illustrated in FIGS. 9 and 10, the secondary pinion gears 407 interengage the respective racks 347 upon assembly of the worm gear housing 301 and barrel housing 201. The secondary pinion gears 407 and the corresponding racks 347 on the worm gear housing 301 are configured and arranged such that upon pivoting of the pinion member 401 relative to the barrel housing 201, the worm gear housing 301 and corresponding worm gear assembly 306 (i.e., the inner shuttle) are driven to move in a direction opposite the direction of movement of the barrel housing (i.e., longitudinally rearward in the illustrated embodiment). Stated another way, because the worm gear housing 301 and worm gear assembly 306 (i.e., the inner shuttle) are disposed within the barrel housing 201 and is thus moved longitudinally forward with the barrel housing relative to the handle housing 101 upon actuating the slide actuator 41 (and hence the barrel housing) forward, the secondary pinion gears 407 cause the worm gear housing 301 and assembly 306 to move longitudinally forward a distance less than the forward travel distance of the barrel housing. This is visible in FIG. 21 by the gap 129 formed between the barrel housing 201 and the worm gear housing 301 when the barrel housing is moved to its maximum travel position corresponding to the deflected configuration of the catheter shaft 29.

By reducing the longitudinally forward travel of the worm gear housing 301 and assembly 306 (i.e., the inner shuttle) relative to the forward travel of the barrel housing 201 (i.e., the outer shuttle), slack is inhibited from forming in the electrode basket pull wire. As such, the worm gear housing 301 and assembly 306 (i.e., the inner shuttle) along with the secondary pinion gears 407 together broadly define a compensator assembly to which the electrode basket pull wire 39 (i.e., the control line) is operatively coupled and is responsive to actuation of the slide actuator 41 (and hence deflection of the catheter shaft 29) to inhibit slack from forming in the electrode basket pull wire. However, the worm gear housing 301 and assembly 306 must move forward some distance along with the barrel housing 201 to avoid increasing tension in the electrode basket pull wire 39 to a tension that would unintentionally expand the electrode basket. It is understood that in other embodiments a suitable compensator assembly other than a shuttle and pinion gear arrangement may be used to inhibit slack from forming in the electrode basket pull wire (i.e., the control line), as long as the compensator is responsive to actuation of the slide actuator 41 (i.e., deflection of the catheter shaft 29) to inhibit slack from forming in the electrode basket pull wire.

In one embodiment, the difference between the barrel housing 201 travel and the worm gear housing 301 travel is at least in part a function of the gear ratio between the primary pinion gear 405 and the secondary pinion gears 407, e.g., in view of the respective distances of the gears from the pivot axis Z of the pinion member 401. For example, in the illustrated embodiment the primary pinion gear 405 is suitably spaced from the pivot axis Z a distance greater than the distance of the secondary pinion gears 407 from the pivot axis. It is understood, however, that the gear ratio may be other than as described above without departing from the scope of this disclosure, as long as it is sufficient to inhibit slack from forming in the electrode basket pull wire 39.

With reference now to FIGS. 7, 8 and 22-27, in one embodiment, the catheter 23 and more particularly the catheter shaft 29 is suitably connected to the handle 25 by a collar 131 (broadly a connector) and flex relief member 133. It is understood, however, that the flex relief member 133 may be omitted without departing from the scope of this disclosure. As illustrated in FIGS. 24-27, the collar 131 is generally tubular, having a frustoconical outer surface 135 tapering inward in cross-section from a longitudinally rear end 137 to a front end 139 thereof, and a central channel 141 extending the length of the collar and defining an inner surface of the collar. The central channel 141 includes a first segment 143 extending longitudinally from the front end 139 of the collar 131 and having a relatively greater transverse cross-section (i.e., diameter) to define a chamber for receiving the catheter shaft 29 into the collar, and a second segment 145 extending longitudinally from the rear end 137 of the collar and having a substantially smaller transverse cross-section than the first segment of the channel. A shoulder 147 is formed within the channel 141 by the reduced cross-section from the first to the second channel segments 143, 145 to thereby define a seat against which one end (i.e., the rear end) of the catheter shaft 29 abuts upon insertion of the catheter shaft into the collar 33 as illustrated best in FIGS. 7, 8 and 27.

In the illustrated embodiment, the first segment 143 of the channel 141 within collar 131 increases gradually (i.e., tapers outward) in transverse cross-sectional dimension (e.g., diameter) from the seat 147 to the front end 139 of the collar. More particularly, the diameter of the channel 141 at the seat 147 against which the shaft 29 abuts is substantially sized relative to the outer diameter of the catheter shaft to facilitate a close contact of the catheter shaft against the inner surface of the collar when the shaft abuts against the seat within the channel. Gradually increasing the transverse cross-sectional dimension of the channel 141 as it extends toward the front end 139 of the collar 131 provides a small clearance between the catheter shaft and the inner surface of the collar along a segment of the collar channel.

A port 149 is formed in and extends transversely through the sidewall of the collar 131 intermediate the front and rear ends 139, 137 of the collar, and more particularly at location along the channel segment where this is a small clearance between the inner surface of the collar and the outer surface of the catheter shaft. Upon assembly of the catheter shaft 29 with the collar 131, the catheter shaft is inserted longitudinally inward into the collar channel 141 at the front end 139 of the collar until the end of the catheter shaft abuts against the seat 147 formed within the channel. A suitable adhesive, such as a UV adhesive, is injected through the fill port 149 into the channel 141. The adhesive flows at least circumferentially around the outer surface of the catheter shaft 29 and in some embodiments also longitudinally within the segment of the channel 141 to fill the spacing between the catheter shaft outer surface and the relatively wider portion of the channel near the front end 139 of the collar (as well as some portions of the channel rearward of the fill port) to provide a circumferential bond between the collar and the catheter shaft. A uniform fill is controlled by the adhesive dispensing time. The collar 131 is suitably constructed of a material that permits the throughpassage of UV energy, such as a polycarbonate or other suitable material, to facilitate curing of the UV adhesive within the collar.

Figure 27:
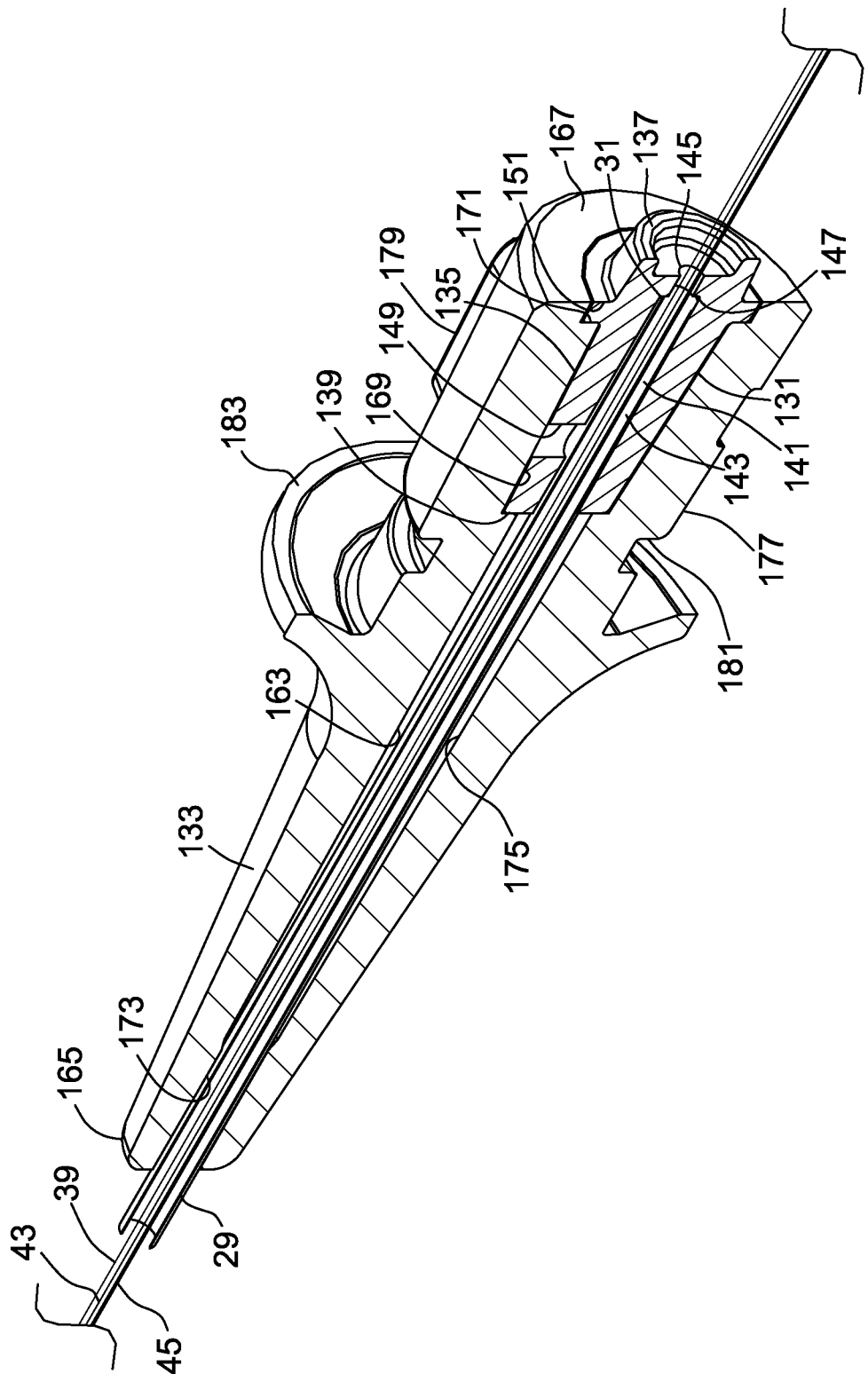
FIG. 27 is a perspective cross-section of the flex relief member and shaft collar with the catheter shaft connected thereto.

An annular flange 151 circumscribes the outer surface 135 of the collar 131 longitudinally inward from the rear end 137 of the collar, and more particularly at a location corresponding generally to the seat 147 formed within the collar channel 141. The flange 151 provides a stop for limiting longitudinal insertion of the collar 131 into the flex relief member 133 as best illustrated in FIGS. 7, 8 and 27. A pair of longitudinally extending flanges 153 (each broadly defining a projection) extend on the outer surface 135 of the collar 131 from the annular flange 151 to the front end 139 of the collar on opposite sides of the collar. These longitudinally extending flanges 153 are received in corresponding grooves 161 (FIGS. 22 and 23) of the flex relief member 133 as described in further detail below upon insertion of the collar 131 into the flex relief member to inhibit rotation of the collar (i.e., to provide torque resistance) relative to the flex relief member.

It is understood that a projection extending outward from the outer surface 135 of the collar 131 may be configured other than as a longitudinally extending flange 153, such as in the form of a post or other suitable projection. It is also contemplated that a single projection, or more than two projections, may be used within the scope of this disclosure. It is also understood that the catheter shaft 29 may be connected to the handle 25 in another suitable manner without departing from the scope of this disclosure.

Figure 22:
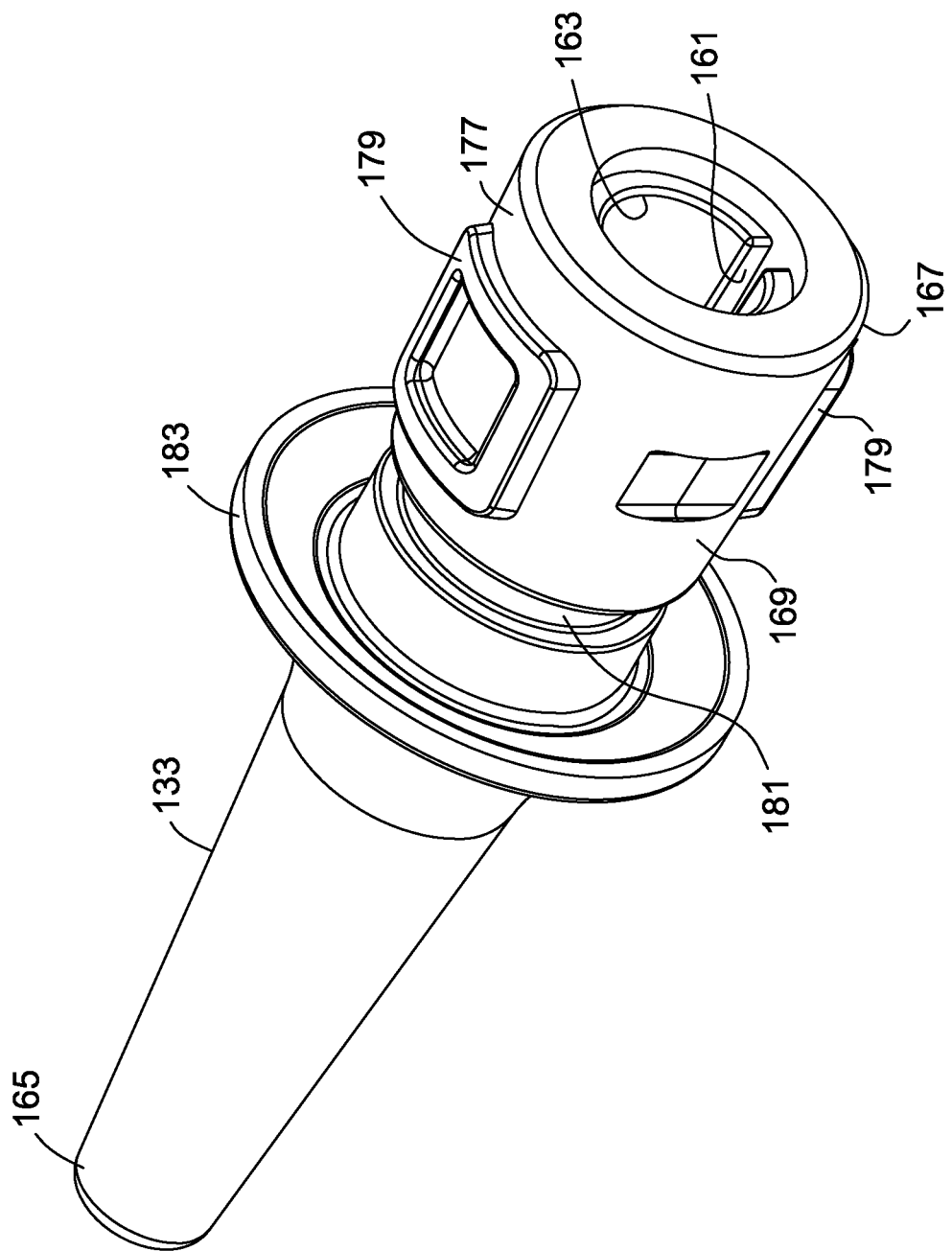
FIG. 22 is a perspective view of a flex relief member of the handle of the catheter system of FIG. 1.
Figure 23:
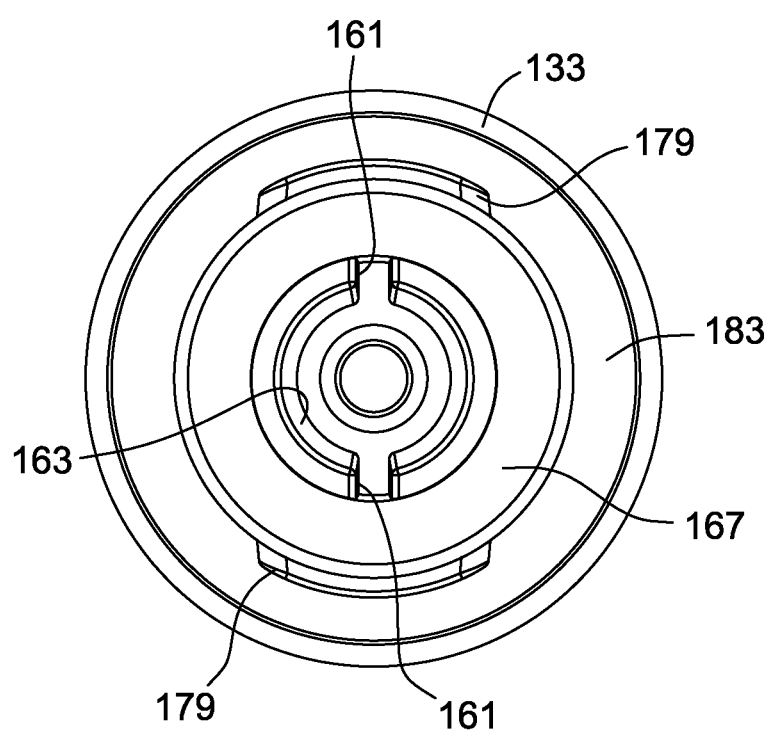
FIG. 23 is a rear elevation thereof.
Figure 24:
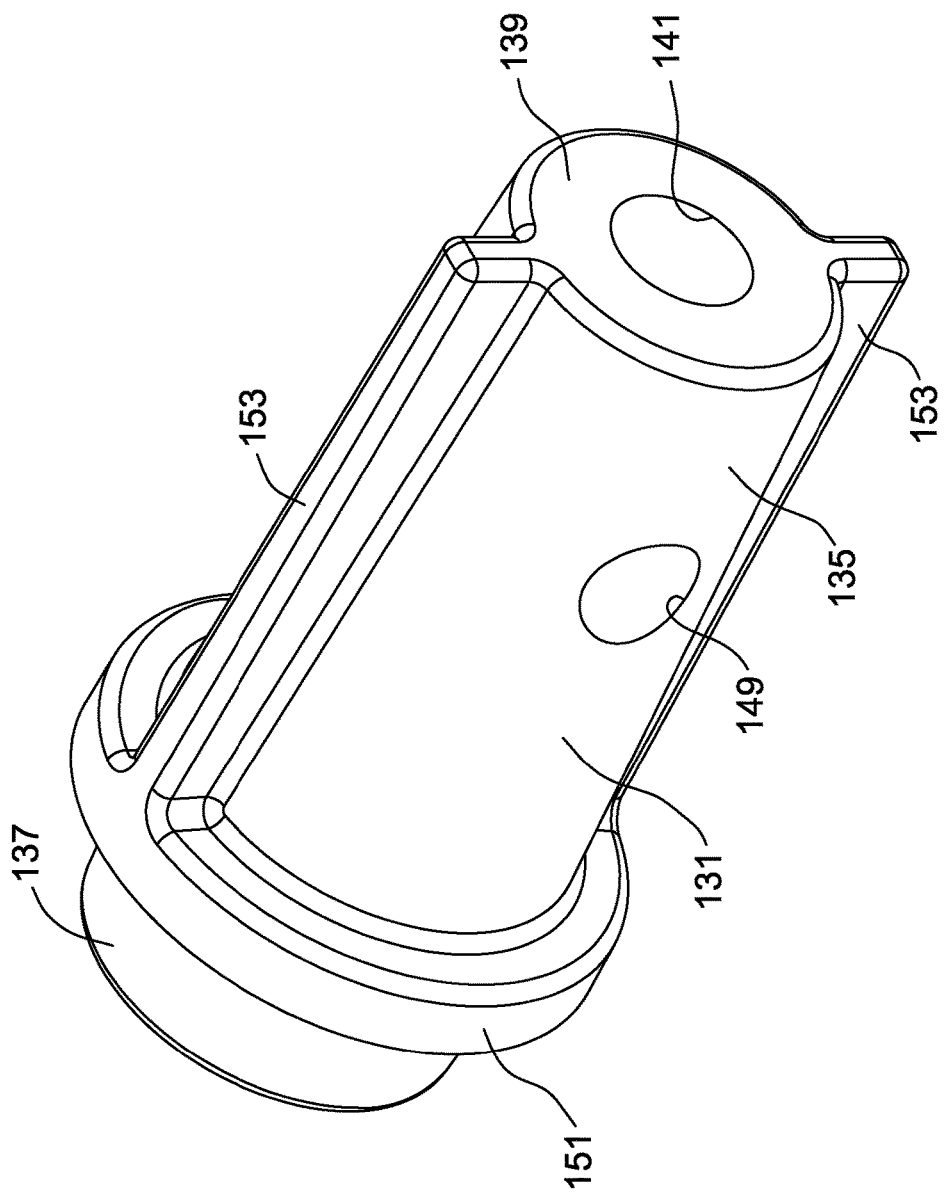
FIG. 24 is a perspective view of a shaft collar of the handle of the catheter system of FIG. 1.
Figure 25:
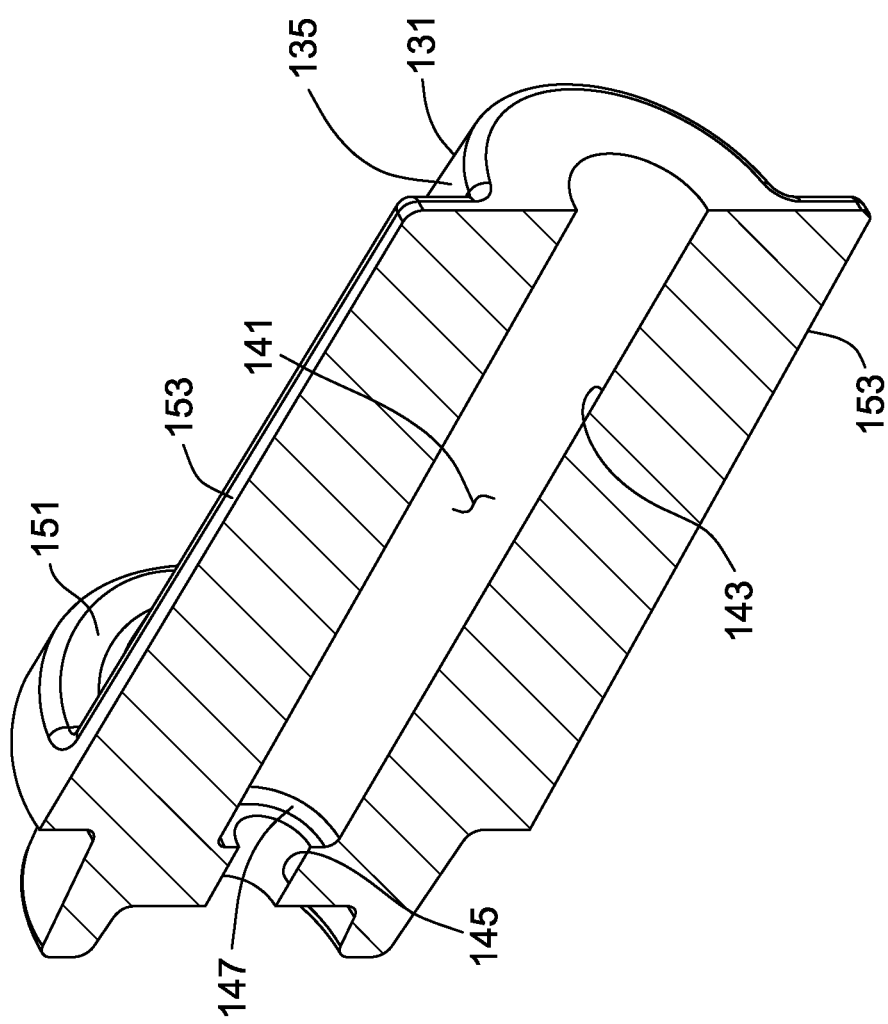
FIG. 25 is a cross-section thereof.
Figure 26:
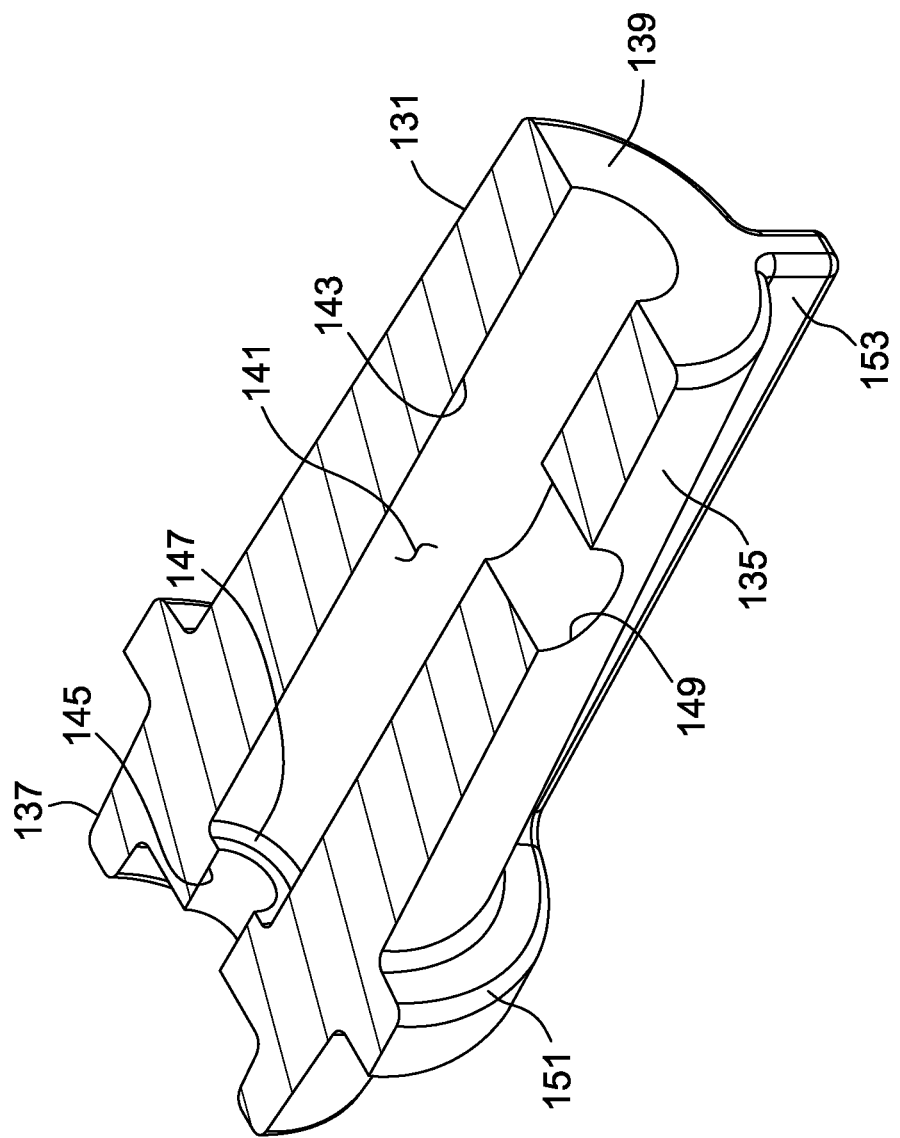
FIG. 26 is a cross-section thereof taken normal to the cross-section of FIG. 22.

With reference to FIGS. 22, 23 and 27, the flex relief member 133 is generally tubular, having a central channel 163 extending the length of the flex relief member, e.g., from an open front end 165 to an open rear end 167 of the flex relief member. The central channel 163 of the illustrated flex relief member 133 comprises three particular segments. A collar housing segment 169 of the channel 163 extends longitudinally forward from the rear end 167 of the flex relief member 133, and is configured in accordance with the outer surface of the collar 131 so as to receive the collar into the collar housing segment in a generally close fitting relationship with the flex relief member (see, e.g., FIG. 27). A seat 171 is formed generally at the rear end 167 of the flex relief member 133 to accommodate the annular flange 151 of the collar 131 to thereby facilitate proper longitudinal insertion of the collar into the flex relief member.

A grip segment 173 of the flex relief member channel 163 extends inward from the open front end 165 of the flex relief member 133 and is sized in transverse cross-section (e.g., diameter) for a close contact fit with the catheter shaft 29 within the flex relief member. In this manner, the catheter shaft 29 is inhibited against flexing at or near the collar 131 so as to inhibit the catheter shaft from being inadvertently disconnected or pulled out from the collar. An intermediate segment 175 of the flex relief member channel 163 extends longitudinally between the grip segment 173 and the collar housing segment 169 and is sized in transverse cross-section relatively larger than the cross-section of the catheter shaft 29. However, it is contemplated that the intermediate segment 175 could be sized for a closer fit of the catheter shaft 29 with the flex relief member 133 along this segment of the channel 163.

A mounting portion 177 of the flex relief member 133 is configured adjacent the rear end 167 thereof for being clamped by the barrel housing 201 of the handle 25 to retain the flex relief member on the handle. The illustrated mounting portion 177 includes a pair of generally square rib elements 179 disposed on opposite sides of the flex relief member 133. Corresponding pockets 229 (FIGS. 15 and 16) are disposed in the barrel housing 201 adjacent the front end 215 thereof for receiving the square rib elements 179 of the flex relief member 133. This facilitates alignment of the flex relief member 133 in the barrel housing 201 and inhibits rotation of the flex relief member relative to the barrel housing following assembly of the handle 25. An annular groove 181 is formed in the outer surface of the flex relief member 133 at the front end of the mounting portion 177 to receive a transversely inward extending flange 231 disposed at the front end 215 of the barrel housing 201 as illustrated best in FIGS. 7 and 8 to thereby positively retain the flex relief member on the barrel housing.

A generally frustoconical closure member 183 circumscribes the flex relief member 133 forward of the mounting portion 177 and is sized in transverse cross-section to seat within the front end of the slide actuator 41 to generally close the front end of the handle 25 upon assembly of the handle to thereby inhibit dirt or other debris from getting into the handle.

Figure 28:
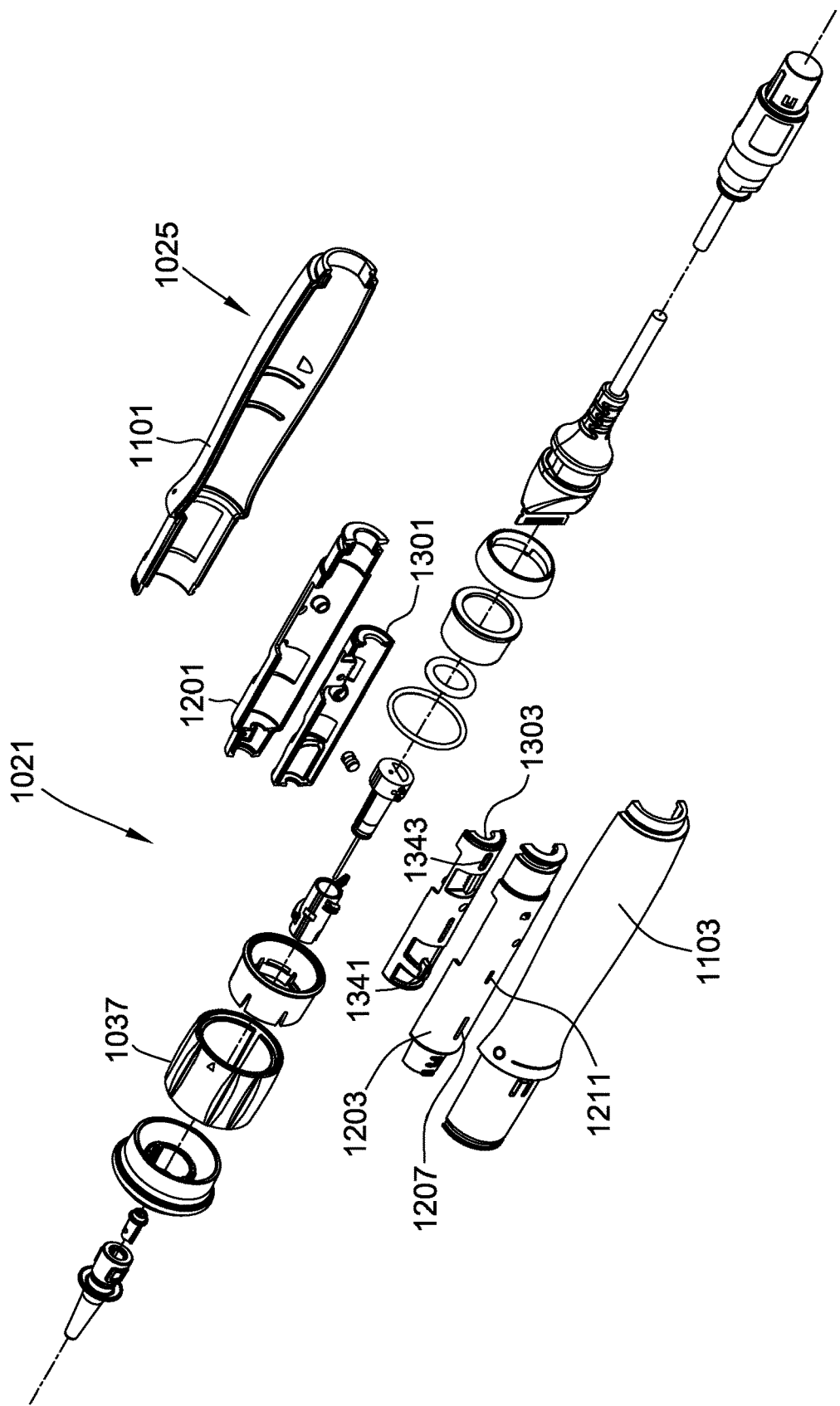
FIG. 28 is an exploded view of a handle of a second embodiment of a catheter system.
Figure 29:
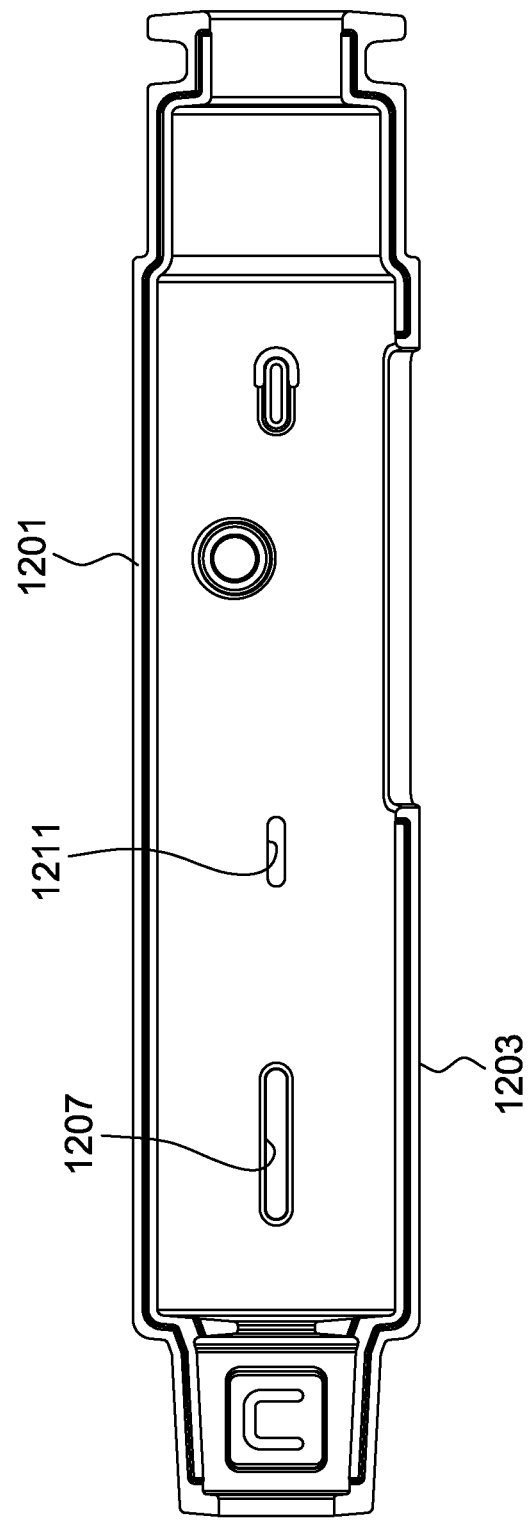
FIG. 29 is a bottom plan view of a top half of a barrel housing of the handle of FIG. 28.

FIGS. 28 and 29 illustrate a second embodiment of a catheter system 1021 generally similar to the catheter system 21 with the electrode basket (not shown but similar to the electrode basket 33 of the embodiment of FIGS. 1-17) being configurable between its collapsed and expanded configurations upon rotation of an annular (e.g., ring-shaped) actuator 1037 relative to a handle 1025 of the catheter system. In this embodiment, however, the catheter shaft (not shown but similar to the catheter shaft 29 of the embodiment of FIGS. 1-27) is retained against deflection near the front end of the catheter shaft.

In this embodiment, the top half 1203 of the barrel housing 1201 includes a guide slot 1207 for receiving a locating tab 1341 (FIG. 28) that projects radially outward from the outer surface of the top half 1303 of the worm gear housing 1301. This guide slot 1207 is sized in length to accommodate sliding movement of the locating tab 1341—and hence the worm gear housing 1301—relative to the barrel housing 1201. A second locating tab (not shown but similar to the locating tab 209 illustrated in FIG. 15) extends radially inward from the inner surface of the top half 1203 of the barrel housing 1201—in longitudinally spaced relationship with the guide slot 1207—and is receivable in a corresponding slot 1343 (FIG. 28) in the top half 1303 of the worm gear housing 1301. A third locating tab (not shown) extends radially inward from the inner surface of the top half 1103 of the handle housing 1101 and is receivable in a corresponding slot 1211 (FIGS. 28 and 29) in the top half 1203 of the barrel housing 1201. Locating the various tabs within the corresponding slots in this manner inhibits relative rotation of the respective housings following assembly of the handle 1025.

As best illustrated in FIG. 29, in this embodiment the slot 1211 that receives the third locating tab (not shown) extending radially inward from the top half 1103 of the handle housing 1101 is substantially shorter in length than the slot 211 of the embodiment of FIGS. 6 and 15. The shortened slot 1211 inhibits the barrel housing 1201 against sliding movement relative to the handle housing 1101 so that no angular deflection of the front end of the catheter shaft can occur. As a result, the pull wire 43 of the embodiment of FIGS. 1-27 that controls deflection of the front end of the catheter shaft is omitted from this embodiment. The pinion gear 401 of the embodiment of FIGS. 1-27 is also omitted from this embodiment.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A catheter system comprising:
a handle comprising a handle housing, and an inner shuttle disposed within the handle housing;
an elongate hollow shaft having a proximal end connected to the handle and a distal end remote from the handle;
a working component carried by the shaft and having at least one characteristic that is adjustable;
an actuator rotatably mounted on the handle for selectively adjusting at least one characteristic of the working component, wherein the actuator is operatively connected to a radially extending lever disposed within the handle and extending through a window in the inner shuttle; and
a control line extending at least in part within the shaft, the control line operatively coupling the actuator with the working component such that rotation of the actuator relative to the handle effects linear translation of the control line to adjust the at least one characteristic of the working component, wherein the working component comprises an electrode basket adjustable between a collapsed configuration and an expanded configuration, wherein rotating the actuator in a first direction drives rotation of the lever within the window of the inner shuttle to thereby increase tension on the control line, causing the electrode basket to transition from the collapsed configuration to the expanded configuration, and wherein rotating the actuator in a second direction drives rotation of the lever within the window of the inner shuttle to thereby release tension on the control line, causing the electrode basket to transition from the expanded configuration to the collapsed configuration.

2. The catheter system of claim 1, wherein the handle has a longitudinal axis, the system comprising a worm gear disposed longitudinally within the handle and being rotatable and longitudinally displaceable relative thereto in response to rotation of the worm gear, the actuator being operatively coupled to the worm gear for driving rotation of the worm gear relative to the housing upon rotation of the actuator, the control line being operatively coupled to the worm gear such that upon linear translation of the worm gear in response to rotation thereof the control line is translated to adjust the at least one characteristic of the working component.

3. The catheter system of claim 2, wherein the worm gear comprises a barrel and the lever, wherein the lever extends radially outward from the barrel.

4. The catheter system of claim 1, wherein the electrode basket comprises a multiple electrode basket.

5. A method of controlling a catheter system of the type having a handle and a working component operatively coupled to the handle by a control line, the method comprising:
rotating an actuator relative to the handle, and
acting on the control line in response to rotation of the actuator using a lever disposed within the handle and operatively coupled the actuator through a window of an inner shuttle disposed within an outer housing of the handle, to effect linear translation of the control line, the linear translation of the control line adjusting at least one characteristic of the working component, wherein the working component is an electrode component basket adjustable between a collapsed configuration and an expanded configuration, the control line being operatively coupled to the electrode basket such that rotation of the actuator in a first direction drives rotation of the lever within the window to thereby increase tension on the control line, causing the electrode basket to transition from the collapsed configuration to the expanded configuration, and such that rotating the actuator in a second direction drives rotation of the lever within the window to thereby release tension on the control line, causing the electrode basket to transition from the expanded configuration to the collapsed configuration.

6. The method set forth in claim 5, wherein the handle has a longitudinal axis, the step of acting on the control line comprising rotating a worm gear disposed within the handle in response to rotation of the actuator whereby rotation of the worm gear effects longitudinal movement of the worm gear relative to the handle, the control line being operatively coupled to the worm gear such that longitudinal movement of the worm gear effects linear translation of the control line to adjust the at least one characteristic of the working component.

7. The method set forth in claim 6, wherein rotating the worm gear comprises rotating the lever of the worm gear in response to rotation of the actuator, the lever extending radially outward from a barrel of the worm gear to conjointly rotate the worm gear relative to the handle in response to rotation of the lever by the actuator.

8. The method set forth in claim 5, wherein the electrode basket comprises a multiple electrode basket.

* * * * *